United States Patent [19]

Farrington, Jr. et al.

[11] Patent Number: 4,614,679

[45] Date of Patent: Sep. 30, 1986

[54] DISPOSABLE ABSORBENT MAT STRUCTURE FOR REMOVAL AND RETENTION OF WET AND DRY SOIL

[75] Inventors: Theodore E. Farrington, Jr., Milford, Me.; Milton D. Spahni, Okeana; Thomas Rattray, Cincinnati, both of Ohio

[73] Assignee: The Procter & Gamble Company, Cincinnati, Ohio

[21] Appl. No.: 549,066

[22] Filed: Nov. 7, 1983

Related U.S. Application Data

[63] Continuation-in-part of Ser. No. 444,935, Nov. 29, 1982, abandoned.

[51] Int. Cl.$^4$ .............................................. B32B 3/10
[52] U.S. Cl. ..................................... 428/138; 15/215; 15/216; 428/131; 428/137; 428/156; 428/158; 428/160; 428/171; 428/172; 428/284; 428/286; 428/343; 428/354; 428/355; 428/423.1; 423.1, 355; 428/423.1, 913; 15/215, 216
[58] Field of Search ............... 428/131, 137, 138, 156, 428/158, 160, 167, 171, 172, 284, 343, 354, 913, 423.1, 355; 428/423.1, 913

[56] References Cited

U.S. PATENT DOCUMENTS

| | | | |
|---|---|---|---|
| 2,251,372 | 8/1941 | Nicholson | 154/49 |
| 2,282,672 | 5/1942 | Nelson | 15/215 |
| 2,826,778 | 3/1958 | Highlen | 15/215 |
| 3,083,393 | 4/1963 | Nappi | 15/215 |
| 3,141,522 | 7/1974 | Fitzpatrick | 184/106 |
| 3,159,502 | 12/1964 | Menin | 117/121 |
| 3,168,757 | 2/1965 | Preston et al. | 15/217 |
| 3,264,167 | 8/1966 | Sands | 161/111 |
| 3,377,643 | 4/1968 | Teng | 15/118 |
| 3,496,054 | 2/1970 | Baigas, Jr. | 161/63 |
| 3,517,407 | 6/1970 | Wyant | 15/215 |
| 3,560,601 | 2/1971 | Johnson et al. | 264/93 |
| 3,696,459 | 10/1972 | Kucera et al. | 15/104.92 |
| 3,717,897 | 2/1973 | Amos et al. | 15/215 |
| 3,785,102 | 1/1974 | Amos | 52/173 |
| 3,804,699 | 4/1974 | Johnson | 161/39 |
| 3,856,610 | 12/1974 | Bruneel | 161/43 |
| 3,945,386 | 3/1976 | Anczurowski et al. | 128/287 |
| 4,096,311 | 6/1978 | Pietreniak | 428/289 |
| 4,143,194 | 3/1979 | Wihksne | 428/81 |
| 4,293,604 | 10/1981 | Campbell | 428/296 |
| 4,328,275 | 5/1982 | Vargo | 428/156 |

Primary Examiner—James J. Bell
Attorney, Agent, or Firm—E. Kelly Linman; John V. Gorman; Richard C. Witte

[57] ABSTRACT

A disposable absorbent structure for the removal and retention of moisture and/or particulate from a soiled object coming in contact therewith. The structure preferably comprises a macroscopically patterned, three-dimensionally expanded, shear resistant uppermost layer having an object contacting surface and a non-object contacting surface, said uppermost layer exhibiting a pattern of protuberances extending upwardly from a first plane and terminating in a second plane substantially parallel to and remote from the first plane. The uppermost layer further exhibits a multiplicity of discrete apertures in its second plane and is pervious to moisture in its first plane. A moisture absorbent substrate having its uppermost surface coextensive with the uppermost object contacting layer is secured substantially continuously to substantially all of the non-object contacting surface of the uppermost layer. The discrete apertures located in the second plane of the uppermost layer expose the subjacent portions of the moisture absorbent substrate directly to the soiled object when the disposable absorbent structure contacts the object. Under normal use conditions, the portions of the uppermost layer initially located in the first plane and the portions of the uppermost layer initially located in the second plane undergo resilient deformation to move closer toward one another, but do not become coplanar with one another when subjected to compressive loads. When the compressive loads are removed, they move in the direction of their initial positions. Absorbent structures of the present invention function to transfer moisture and/or particulate from a soiled object into the moisture absorbent substrate via the discrete apertures in and/or the moisture-pervious portions of the uppermost layer of the structure. Once moisture and particulate enter the moisture absorbent substrate, they are effectively isolated from objects coming in contact with the structure by the uppermost object contacting layer.

54 Claims, 16 Drawing Figures

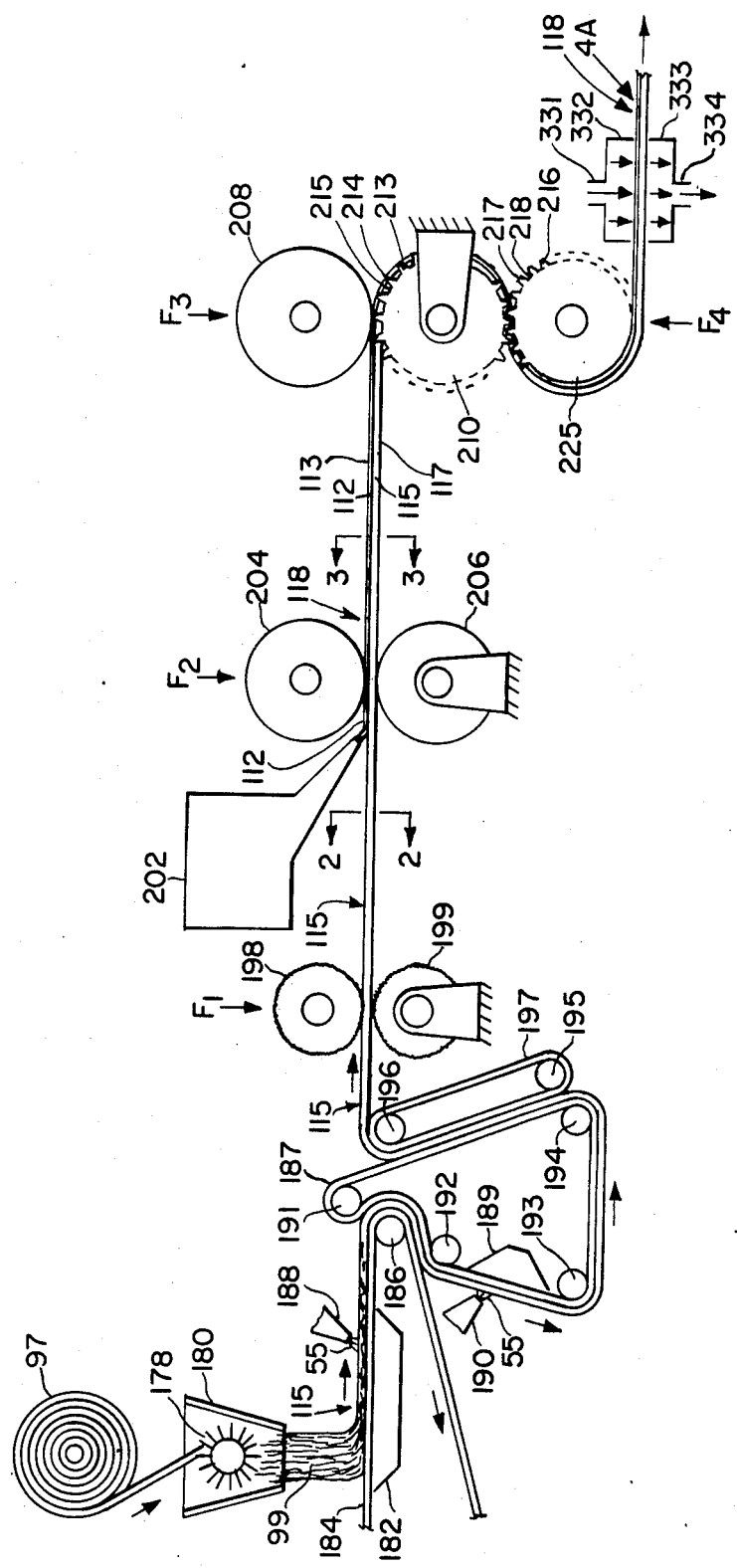

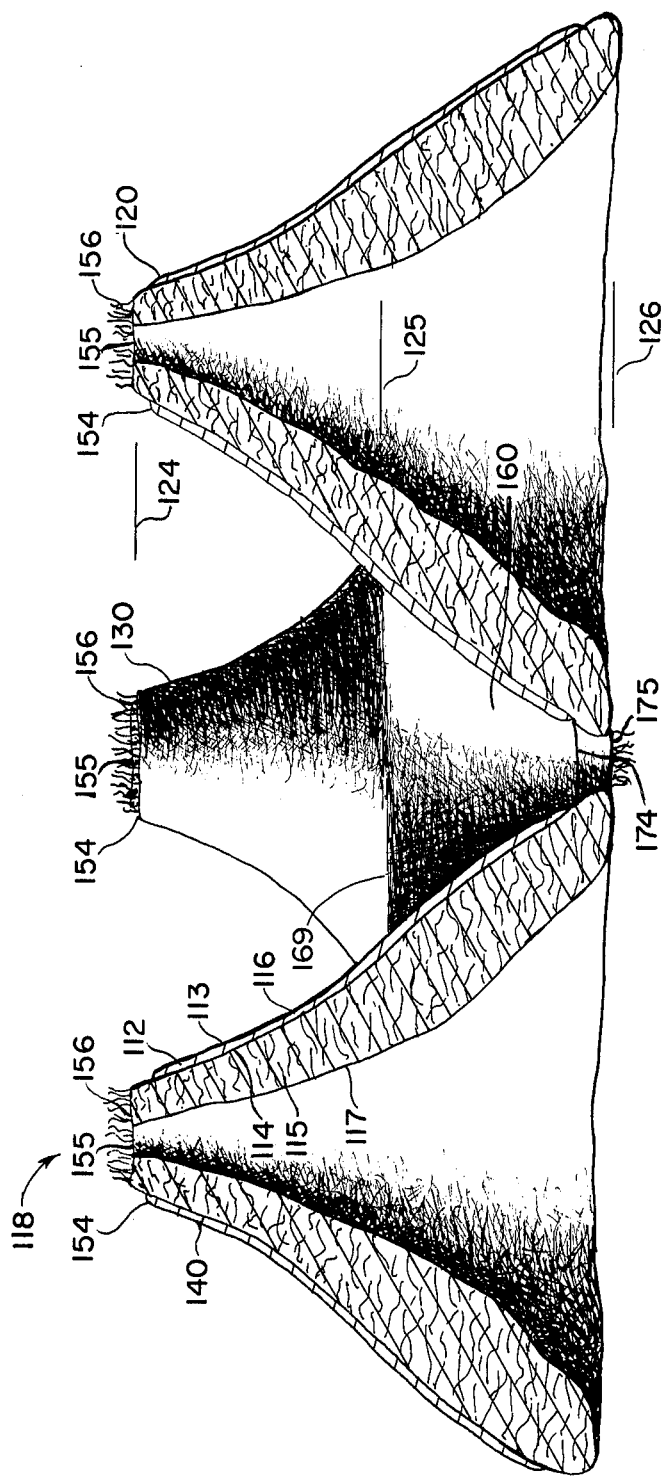

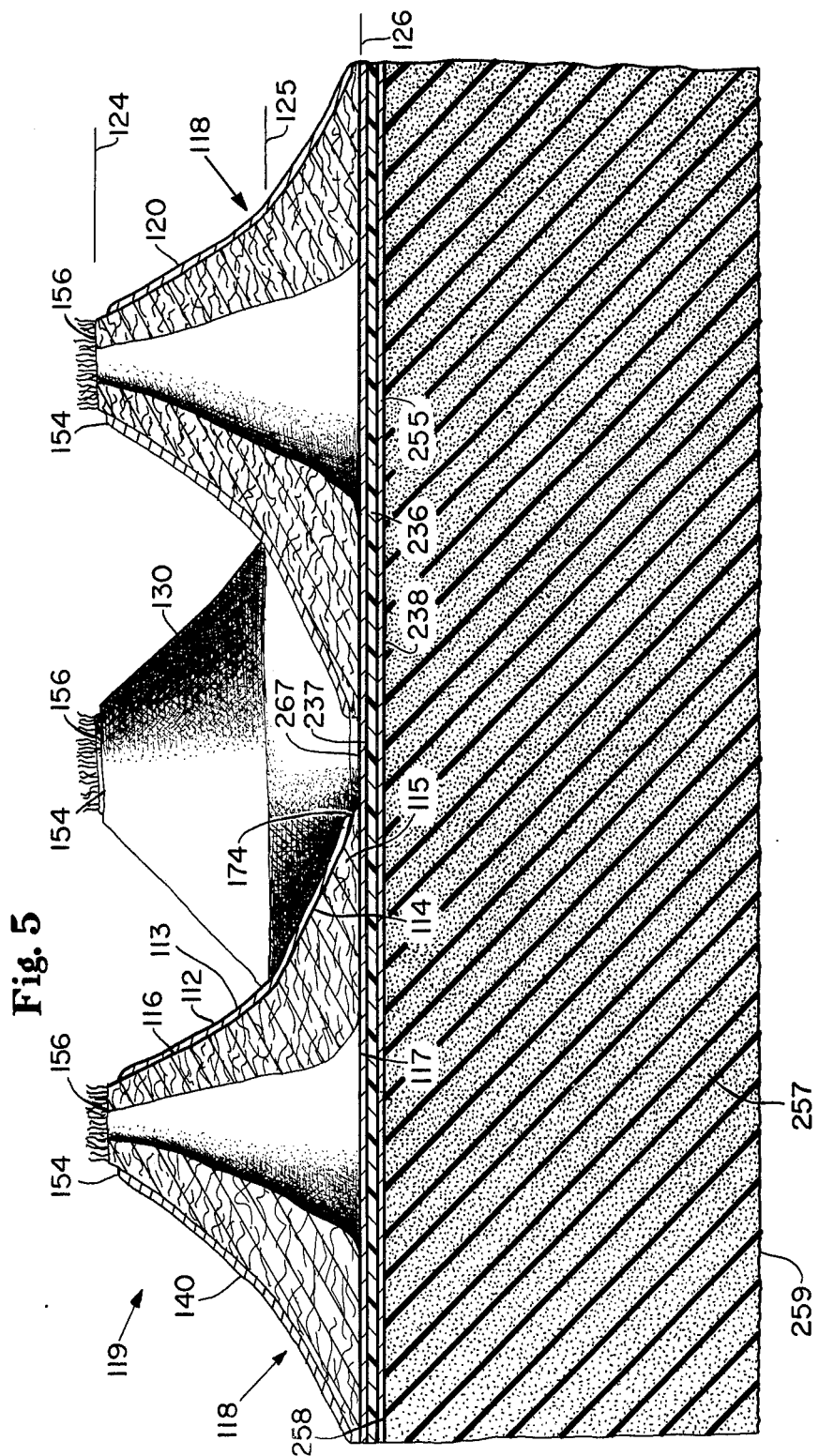

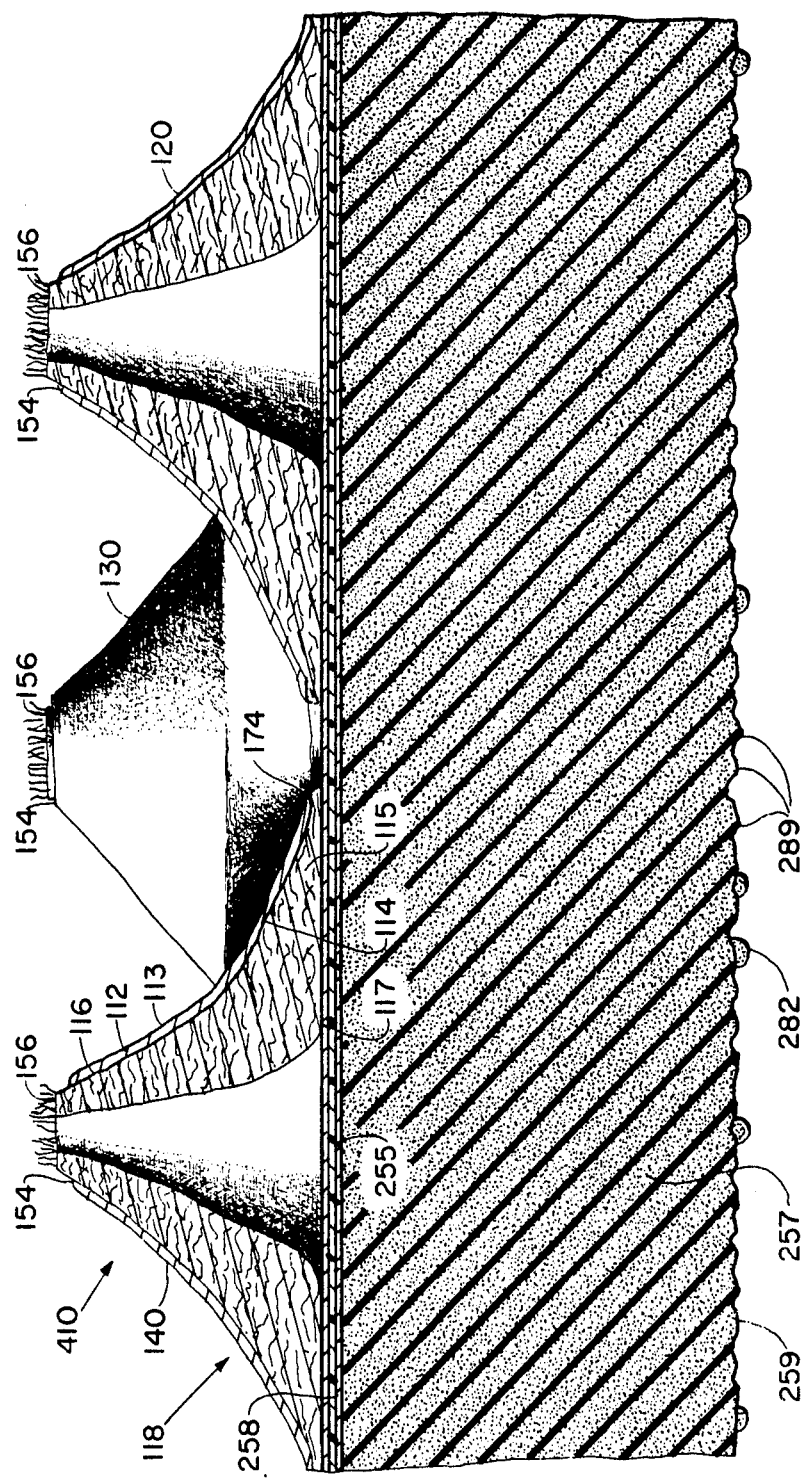

DISPOSABLE ABSORBENT MAT STRUCTURE FOR REMOVAL AND RETENTION OF WET AND DRY SOIL

CROSS-REFERENCE TO RELATED APPLICATION

This application is a continuation-in-part of co-pending application Ser. No. 06/444,935 filed Nov. 29, 1982 in the name of the present applicants and now abandoned.

TECHNICAL FIELD

The present invention has relation to a macroscopically patterned, three-dimensionally expanded laminate structure which will remove and retain both moisture and particulate from soiled objects.

The present invention has further relation to a macroscopically patterned, three-dimensionally expanded laminate structure comprising an uppermost or object contacting layer and an absorbent substrate layer secured thereto, said laminate structure exhibiting sufficient structural integrity in its uppermost or object contacting layer to prevent disintegration of the absorbent substrate secured thereto during twisting and wiping.

The present invention has further relation to such a laminate structure which will exhibit sufficient z-direction resilience that it will not collapse to a completely planar condition when contacted by a soiled object under normal standing or walking pressures and which will regain a substantial portion of its original caliper when the soiled object is removed therefrom.

In a preferred embodiment, the present invention relates to such a disposable absorbent structure having a macroscopically patterned, three-dimensionally expanded object contacting layer which exhibits discrete apertures in its uppermost plane and which is pervious to moisture in its lowermost plane to permit particulate to enter directly into the absorbent substrate via the discrete apertures and moisture to enter the absorbent substrate via the discrete apertures and those portions of the uppermost layer which are moisture-pervious in the lowermost plane.

In a particularly preferred embodiment, the present invention relates to such a disposable absorbent structure having a macroscopically patterned, three-dimensionally expanded object contacting layer which exhibits discrete apertures in both its uppermost and lowermost planes to permit moisture and particulate to enter the absorbent substrate located subjacent said object contacting layer through said apertures.

Finally, the present invention has relation to such a structure which provides superior functionality as a low-cost, disposable floor mat.

BACKGROUND ART

In general, both consumers and flooring manufacturers are concerned with the negative impact of soiling on the appearance of floors and carpets. Carpet manufacturers take many steps to minimize the detractive appearance of soils on carpets through careful selection of fibers, soil release finishes, and colors which serve either to make soils easy to remove or hide their presence. Consumers have also employed means to minimize the effect of soiling on their floors and carpets by frequent vacuuming and sweeping to retrieve soils.

Another known means for preserving floor appearance is to trap soils before they are transferred via foot traffic onto permanent floors and carpets. This is typically done with the use of floor mats. To be totally functional, such floor mats need to effectively remove and retain both wet and dry soils, particularly when utilized at entry points from the outdoors.

In many instances, carpet remnants and carpet-like structures are utilized at such entry points and function well to remove dry soils from the shoe surface. However, to provide a satisfactory result, wet soils also need to be absorbed by such mats. The contact time during which this absorption takes place is often very short. Using a normal walking pace of about 100-120 steps per minute, this contact time is typically about 0.5 seconds. In such case, it is desirable that the floor mat have quick enough absorption rates that the wet soils can be absorbed from the bottom of a person's shoes during this short 0.5 second residence time.

Carpet remnants have not always proven totally effective in this regard. To a degree this may be due to the moisture resistant, i.e., hydrophobic, nature of the fibers utilized to manufacture the carpets from which they are cut and to moisture resistant treatments imparted to the carpets by the manufacturers. Furthermore, soils deposited on such carpet remnants are often readily visible, particularly on lighter colored materials, thereby necessitating disposal or at least cleaning of the carpet remnant due to an unsightly appearance long before its absorptive capacity has been reached. Although carpet remnants are relatively inexpensive since they are salvaged from scrap, carpet-like structures specifically manufactured for floor mat applications are typically quite high in cost due to the relatively high cost of the labor and materials required.

Accordingly, numerous efforts have been undertaken in the past to provide a disposable, low cost floor mat which will function effectively to remove and retain wet and dry soil, which will minimize the appearance of objectionable soil on the mat's surface in use, yet which is low enough in cost that it can be readily disposed of as soon as its soil loading capacity has been utilized.

Prior art disposable mat structures intended to remove dry soil are well known in the art. Typically these dry soil removal structures employ one or more substantially planar, adhesive surfaced sheets which serve to contact and secure particulate soils thereto when contacted by a shoe sole or other soiled object. In many instances, the individual adhesive sheets are stacked in multiple layers either directly on the floor surface or indirectly by means of a specially designed holder. Exemplary of such structures are those disclosed in U.S. Pat. No. 4,143,194 issued to Wihksne on Mar. 6, 1979; U.S. Pat. No. 3,785,102 issued to Amos on Jan. 15, 1974; U.S. Pat. No. 3,717,897 issued to Amos et al. on Feb. 27, 1973; and U.S. Pat. No. 3,083,393 issued to Nappi on Apr. 2, 1963. While these structures may work reasonably well for dry particulate soil removal and retention, they are non-absorptive and hence totally ineffective for the removal and retention of wet soil. Furthermore, since these prior art adhesive sheet type structures are substantially planar and relatively incompressible, there is little tendency for the mat structure to deform and allow complete contact with substantially all of the shoe's lowermost surface. Accordingly, only isolated portions of the shoe's lowermost surface are effectively cleaned by such mat structures. Finally, due to the fact that soils transferred from the shoe sole to the mat surface are readily visible because of the impermeable nature of the imperforate adhesive sheets, frequent removal of the uppermost layer and consequently greater cost is associated with the use of such disposable mat structures.

Combination cleansing and sanitizing mat structures are also known in the art. For example, U.S. Pat. No. 3,696,459 issued to Kucera et al. on Oct. 10, 1972 discloses an assembly which is provided with a first area which moistens the soles of the wearer's shoes by utilizing the wearer's weight to dispense a controlled amount of cleaning solution to loosen the dirt. An adjacent second area removes the cleaning solution along with the suspended dirt and dries the shoes. Still another sanitary door mat is disclosed in U.S. Pat. No. 2,282,672 issued to Nelson on May 12, 1942. Nelson discloses a structure in which a disinfectant reservoir is provided with an insert of absorptive material having sufficient mechanical resistivity to clean shoe soles. A liquid disinfectant is typically retained within the reservoir to treat the shoe soles during the soil transfer process. Such structures are, however, typically expensive thereby making the cost of disposal relatively high. Furthermore, the presence of liquid in the reservoirs of such structures makes installation and removal without spillage difficult.

A more recent attempt to reduce the cost of the mat structure and consequently reduce the cost associated with its disposal is disclosed in U.S. Pat. No. 4,328,275 issued to Vargo on May 4, 1982. Vargo discloses a disposable floor mat for use in bathrooms and the like comprising a sheet of liquid absorbent matting having raised portions for supporting a person's feet. These raised portions have a liquid-repellant coating thereon for maintaining the feet relatively dry as liquid falling onto the mat is absorbed by the matting. The raised portions are preferably comprised of cellulose fibers and starch and are characterized as being substantially incompressible. The primary purpose of the mat appears to be the absorption of spilled liquids.

U.S. Pat. No. 3,856,610 issued to Bruneel on Dec. 24, 1974 discloses a floor mat construction wherein an absorbent fibrous substrate is enclosed by a liquid impervious skin such as polyurethane which is adhered to the surface of the absorbent portion. The uppermost surface of the mat is substantially planar and is perforated by a plurality of aligned bores extending a predetermined depth into the absorbent body portion of the mat. The aligned bores are utilized for the absorption of liquid as well as to trap small particulate.

U.S. Pat. No. 3,517,407 issued Wyant on June 30, 1970 discloses a disposable mat made from a paper towel absorbent encapsulated on its lowermost and edge portions by means of a polyethylene sheet and protected on its uppermost surface by means of a woven craft paper yarn to provide abrasion resistance.

Despite the appearance of the aforementioned prior art structures in the patent literature, none of the disclosed embodiments appear to have gained widespread commercial acceptance. It is believed that this is due to the relatively high cost associated with disposal after a relatively short use life, the inability of such structures to effectively remove and retain both dry particulate and wet soil and the unsightly appearance which rapidly develops shortly after these prior art mat structures are placed in service.

Accordingly it is an object of the present invention to provide a low cost disposable absorbent structure which will effectively remove and retain both dry particulate and wet soil from a soiled object coming in contact therewith.

It is a further object of the present invention to provide a structure having a resiliently deformable, macroscopically patterned, three-dimensional, object contacting surface which will deform substantially when contacted by a soiled object to maximize the overall degree of contact with the object, yet which will not collapse into a single plane so as to permit redeposition of transferred soils back onto the object being cleansed when subjected to normal standing or walking pressures.

It is a further object of the present invention to provide, in a particularly preferred embodiment, a structure wherein the bulk of the soils transferred from the soiled object are entrapped and/or absorbed into an absorbent substrate located subjacent the object contacting layer rather than remaining completely visible on the object contacting surface of the structure.

It is a further object of the present invention to provide such a structure wherein the soils transferred from the soiled object are not redeposited onto the surfaces of cleansed objects coming in contact with the object contacting surface of the structure.

Finally, it is an object of the present invention to provide such a structure wherein under normal use conditions, substantially all of the soil storage capacity of the structure may be utilized prior to its disposal without the appearance of said structure becoming objectionable.

DISCLOSURE OF THE INVENTION

The present invention, in a particularly preferred embodiment, pertains to a disposable absorbent structure for the removal and retention of moisture and/or particulate from a soiled object coming in contact therewith. The structure preferably comprises a macroscopically patterned, three-dimensionally expanded, shear resistant uppermost layer having an object contacting surface and a non-object contacting surface, said uppermost layer exhibiting a pattern of protuberances extending upwardly from a first plane and terminating in a second plane substantially parallel to and remote from the first plane. The uppermost layer further exhibits a multiplicity of discrete apertures in its second plane and is pervious to moisture in its first plane. In a preferred embodiment, the uppermost layer also exhibits a multiplicity of discrete apertures in its first plane. In a particularly preferred embodiment, the uppermost layer further exhibits a second pattern of protuberances originating in and extending downwardly from said first plane, said discrete apertures in said first plane defining the base of said protuberances in said second pattern. The protuberances in said second pattern terminate in a third plane substantially parallel to and remote from said first plane. The uppermost layer is also pervious to moisture in said third plane, preferably by means of discrete apertures located at the terminal end of said protuberances in said third plane.

A moisture absorbent substrate having its uppermost surface coextensive with the uppermost or object contacting layer is secured substantially continuously to substantially all of the non-object contacting surface of the uppermost layer. The discrete apertures located in the second plane of the uppermost layer expose the subjacent portions of the moisture absorbent substrate directly to the soiled object when the disposable absorbent structure contacts the object. The uppermost layer of the disposable absorbent structure and the portions of the absorbent substrate secured thereto are resiliently deformable to permit the portions of the uppermost layer normally located in the second plane to move closer to the portions of the uppermost layer normally located in the first plane when the absorbent structure and the soiled object contact one another. Under normal use conditions the portions of the uppermost layer initially located in the first plane and the portions of the uppermost layer initially located in the second plane do not, however, become coplanar with one another upon contact by the soiled object, as this would facilitate redeposition of soil, particularly particulate soil, initially transferred from the object to the disposable absorbent structure.

From the foregoing, it necessarily follows that in those embodiments of the present invention wherein a third plane is also formed by protuberances in the uppermost layer, those portions of the uppermost layer initially located in the second plane will not become coplanar with those portions of the uppermost layer initially located in said third plane.

After the object has been separated from the disposable absorbent structure, the first plane, the second plane and the third plane (when present) defined by the uppermost or object contacting layer of the structure and those portions of the absorbent substrate secured thereto return a substantial portion of the way to their original positions and hence toward their original distance of separation. Thus absorbent structures of the present invention function to transfer moisture and/or particulate from a soiled object into the moisture absorbent substrate via the discrete apertures in and/or the moisture pervious portions of the uppermost layer of the structure. Once moisture and particulate enter the moisture absorbent substrate, they are effectively isolated from objects coming in contact with the structure by the uppermost object contacting layer.

In a preferred embodiment, the disposable absorbent structure includes a moisture resistant barrier secured in subjacent relation to the lowermost surface of the moisture absorbent substrate. When the present invention is practiced as a disposable absorbent floor mat, the aforementioned moisture resistant barrier may comprise a layer of moisture impermeable polymeric film secured subjacent the lowermost surface of the moisture absorbent substrate.

In a particularly preferred embodiment, a layer of resilient material such as open celled polymeric foam is secured to the lowermost surface of the moisture resistant barrier to promote overall conformance of the mat to the shoe sole and to prevent slipping of the mat, particularly on carpeted surfaces.

BRIEF DESCRIPTION OF THE DRAWINGS

While the specification concludes with claims particularly and distinctly claiming the present invention, it is believed the present invention will be better understood from the following description in conjunction with the accompanying drawings in which:

FIG. 1A is a simplified schematic illustration of a preferred process for producing a disposable absorbent structure of the present invention;

FIG. 4B is a greatly enlarged simplified cross-section of the web generally illustrated in FIG. 4A, said cross-section being taken generally along section line 4B—4B of FIG. 4A;

FIG. 5 is a greatly enlarged simplified cross-section taken along section line 5—5 of FIG. 1B;

FIG. 6 is a cross-sectional view of the web shown in FIG. 5 after a floor stabilizing pressure sensitive adhesive has been applied to its lowermost surface, said cross-section being taken generally along section 6—6 of FIG. 1B;

DETAILED DESCRIPTION OF THE INVENTION

Figure 1B:
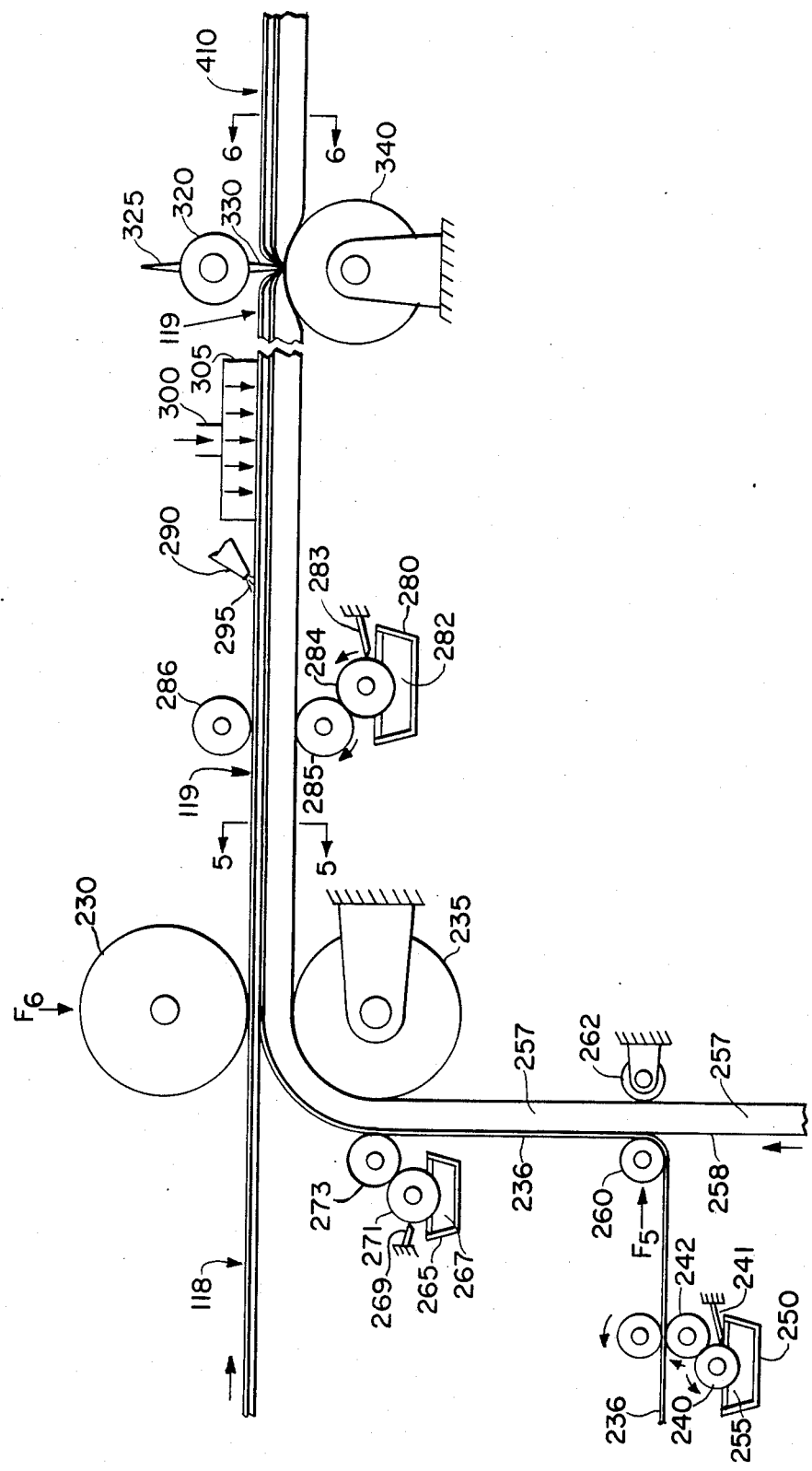
FIG. 1B is a simplified schematic illustration of a preferred process for incorporating the disposable absorbent structure disclosed in FIG. 1A into a disposable absorbent floor mat.

FIG. 1A is a simplified schematic illustration of a particularly preferred process for making a disposable absorbent structure which will effectively remove and retain both moisture and particulate from a soiled object which comes in contact therewith. While such structures may be utilized to advantage when only the uppermost and absorbent substrate layers are present, the process generally illustrated in FIG. 1B discloses means for applying a moisture impermeable barrier layer, a resilient substrate and a floor stabilizing agent thereto to provide a disposable absorbent floor mat which represents a particularly preferred embodiment of the present invention.

In the preferred process generally illustrated in FIGS. 1A and 1B, fibrous dry lap such as is conventionally utilized in airlaid absorbent cores for structures such as disposable diapers is preferably utilized as a starting material for the absorbent substrate. A roll of fibrous dry lap 97 is fed into a rotary disintegrator 178 such as is well known in the art. The disintegrator 178 reduces the incoming dry lap 97 to a multiplicity of discrete fibrous elements 99 and introduces them into an airstream within the confines of the disintegrator housing 180. The individual fibrous elements 99 are thereafter collected on a continuous, travelling foraminous belt 184 rotating about pulley 186 by drawing the air in the fiber filled airstream through the foraminous belt 184 by means of a vacuum chamber 182 located subjacent said belt. Means for forming airlaid fibrous webs are well known in the art and therefore not shown in great detail in FIG. 1.

After formation of an airlaid fibrous web 115 on foraminous belt 184, a liquid latex 55 is preferably applied to the uppermost surface of the web. In the embodiment illustrated in FIG. 1A, this is done by means of a nozzle 188 having a spray pattern which extends across the width of the web. Printing or other means well known in the art may be employed for this purpose with equal facility. If desired, the web may be subjected to suction during the spraying operation to draw the liquid latex 55 deeply into the web structure.

Once sufficient cohesive strength has been imparted to the airlaid web, the lowermost surface of the web is also preferably subjected to a similar liquid latex treatment, e.g., spraying by means of nozzle 190 as the web is conveyed on foraminous belt 187 operating about pulleys 191, 192, 193 and 194. The latex 55 applied to the lowermost surface of the fibrous web may be the same as latex 55 applied to the uppermost surface of the web. If desired, the uppermost surface of the web may also be subjected to suction by means of vacuum box 189 to cause penetration of latex 55 into the lowermost surface of the web. Once the lowermost surface of the web has been treated with latex 55, the latex impregnated web 115 is transferred to belt 197 operating about pulleys 195 and 196 by means well known in the art.

The latex impregnation treatment of the fibrous web 115 stiffens the exposed fibers and provides cohesive strength to the web so that individual fibers are not readily removed therefrom when they contact a soiled object in use. In addition, the latex impregnation treatment imparts integrity and shear resistance to the web so that it does not readily disintegrate when the composite structure in which it is ultimately embodied is subjected to shear stresses typically encountered during twisting, wiping or scrubbing operations.

After drying of the latex, as by the application of hot air to the moving web by means well known in the art (and therefore not shown), the impregnated web 115 is preferably subjected to a fine scale embossing operation between a pair of embossing rolls 198 and 199. The degree of embossing imparted to the web 115 will depend upon the pattern employed as well as the magnitude of the force $F_1$ applied to the floating roll 198 as the web passes through the nip formed between rolls 198 and 199.

The embossing operation generally illustrated in FIG. 1A preferably imparts a continuous interconnected pattern of densified areas in the latex impregnated web 115. These densified areas provide increased tensile strength to the web as well as improved moisture transport or wicking properties due to the smaller interstitial capillary structure existing within the densified areas.

Figure 2:
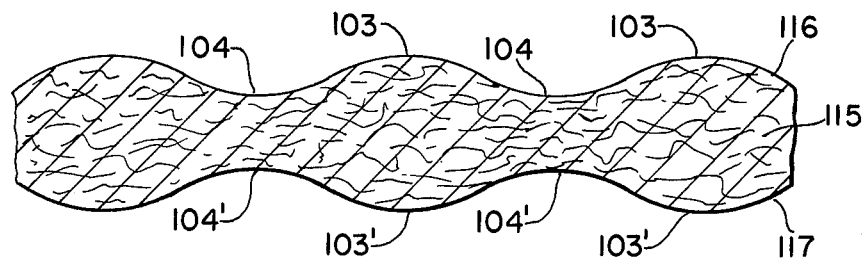
FIG. 2 is an enlarged simplified cross-section taken along section line 2—2 of FIG. 1A showing the airlaid, latex bonded absorbent web after the web has been subjected to a fine scale embossing operation.

A particularly preferred embodiment of the latex impregnated, embossed web 115 is generally shown in FIG. 2, which is taken along section line 2—2 of FIG. 1A. The uppermost surface 116 of the web 115 exhibits a fine scale sinusoidal type of pattern comprising bumps 103 and depressions 104. The depressions 104 correspond to the pressure points on embossing roll 198. The lowermost surface 117 of web 115 also illustrates a pattern of bumps 103' and depressions 104'. The depressions 104' correspond to the pressure points on embossing roll 199. Since the corresponding pressure points on embossing rolls 198 and 199 mate with one another, the depressions 104 in uppermost surface 116 correspond with the depressions 104' in lowermost surface 117, while the bumps 103 in uppermost surface 116 correspond to the bumps 103' in lowermost surface 117. From the foregoing it should be clear that the densified areas of the web correspond with areas 104, 104', while the undensified areas of the web correspond with areas 103, 103'. In a particularly preferred embodiment, the embossing pattern is such that the densified areas 104, 104' are continuously interconnected to one another across the width of the web.

If desired, absorbent materials other than latex impregnated, airlaid fibrous webs may be employed as web 115, provided they exhibit sufficient integrity to prevent disintegration and/or delamination of the resultant laminate structure in use.

In a particularly preferred embodiment, absorbent web 115 comprises an airlaid latex 868 grade web, such as is available from The Fort Howard Paper Company of Green Bay, Wis. The web 115 preferably exhibits a basis weight in the range of about 30 to about 110 pounds per 3000 square feet and a caliper between about 10 and about 45 mils.

Following the fine scale embossing operation shown in FIG. 1A, web 115 is preferably fed into the nip formed between a pair of smooth surfaced compression rolls 204, 206. Just prior to entry into the nip, a molten extrudate 112 of a polymeric material such as polyethylene is preferably extruded by means of extruder 202 onto the uppermost surface 116 of the latex impregnated, embossed absorbent web 115. In a particularly preferred embodiment, the thickness of layer 112 is in the range of about 0.3 mils (0.0003 inches) to about 3.0 mils (0.003 inches). Because the extrudate 112 is in a molten state upon entry into the nip between rolls 204 and 206, the application of a compressive force $F_2$ to floating roll 204 causes the molten extrudate 112 to substantially conform to the undulating uppermost surface 116 of fibrous web 115, thereby causing the projecting fibers on the uppermost surface of the web to entangle with and bond to the lowermost surface 114, also referred to as the non-object contacting surface, of the extrudate 112 as the extrudate cools below its softening temperature. This produces a web 118 which is laminar in nature and which is similar to that generally illustrated in FIG. 3, an enlarged cross-section taken along section line 3—3 of FIG. 1.

Once the molten extrudate 112 has been allowed to cool, the resultant laminate web 118 is thereafter subjected to a macroscopically patterned embossing operation wherein it undergoes three-dimensional expansion. As utilized herein, the term "macroscopically patterned" when used to describe three-dimensionally expanded laminate webs and the like refers to a pattern wherein both surfaces of the layer or web in question exhibit the three-dimensional pattern of the embossing roll or other structure to which it is caused to conform, said pattern being readily visible to the normal naked eye when the perpendicular distance between the viewer's eye and the plane of the web is about 12 inches (30.5 cm.).

In the embodiment illustrated in FIG. 1A, the laminate web 118 is preferably fed into a first nip formed between a smooth surfaced floating roll 208 and a subjacently positioned, macroscopically patterned male embossing roll 210 such that the lowermost surface 117 of the absorbent web 115 contacts the male embossing roll 210 while the uppermost surface 113 of the polymeric extrudate layer 112 contacts the smooth surfaced roll 208. A compressive force $F_3$ is applied to the smooth surfaced floating roll 208 to fix the position of the laminate web 118 relative to the surface of the first male embossing roll 210 prior to carrying out the nested male-to-male embossing operation against mating male embossing roll 225.

The surface of male embossing roll 210 comprises a continuous pattern of protuberances 213 which are preferably uniformly spaced relative to one another across the entire periphery of roll 210. The protuberances 213 may, by way of non-limiting example, be in the form of discrete conical segments, discrete four-sided pyramidal segments, continuously extending straight or curvilinear ribs, concentric circles, or nearly any desired combination thereof.

In the embodiment illustrated in FIG. 1A, discrete conical protuberances 213 are illustrated. A continuous, intersecting pattern of valleys 215 is thus formed intermediate each protuberance 213 and all surrounding protuberances 213. The protuberances 213 terminate at their outermost surface to form relatively small land areas 214. In an exemplary embodiment of the present invention, the embossment pattern comprised a pattern of approximately 64 conical protuberances per square inch, each of said protuberances having a base diameter of approximately 3 millimeters, an overall height between about 0.5 and about 0.75 millimeters, said protuberances being spaced in a close-packed pattern approximately 3 millimeters on centers.

When the embossing operation is performed between hard surfaced embossing rolls, such as is illustrated in the FIG. 1A embodiment, roll 210 must exhibit a pattern which will mesh with the pattern on roll 225. The perimeter of macroscopically patterned male embossing roll 225 is similar to that of male embossing roll 210.

The protuberances 216 on roll 225 are identical to protuberances 213 on roll 210. They are surrounded by a continuous, intersecting pattern of valleys 218 and terminate at their outermost surface to form relatively small land areas 217. Embossing rolls 210 and 225 preferably exhibit identical pitch diameters and are so nested with respect to one another that the protuberances 213 on roll 210 nest within the valleys 218 on roll 225, while the protuberances 216 on roll 225 nest within the valleys 215 on roll 210. As shown in FIG. 1A, roll 225 is preferably a floating roll. The amount of force $F_4$ applied to floating roll 225 and the pattern employed will determine the nature and extent of embossment and aperturing imparted to the laminate web 118 as it passes through the nips formed between rolls 208, 210 and 210, 225, respectively.

It is of course recognized that macroscopic embossing of laminate web 118 and discrete aperturing of uppermost layer 112 could be carried out by means other than hard surfaced mating embossing rolls. For example, one or more hard surfaced embossing rolls could be operated against one or more yieldable surfaced rolls to impart the desired macroscopic embossing pattern to the laminate web. The latter approach may in fact permit greater flexibility in pattern selection since the requirement to provide a mating hard surfaced roll to nest with the first hard surfaced roll is eliminated. Embossing operations of the latter type could be done either in a single or in multiple stages. Also, the discrete aperturing operation for uppermost layer 112 could, if desired, be performed subsequent to the macroscopically patterned embossing operation by other means well known in the art, e.g., exposing the object contacting surface of the web to a laser perforating operation.

A particularly preferred result of the macroscopically patterned embossing operation disclosed in FIG. 1A is exhibited by the three-dimensionally expanded laminate web 118 shown in a perspective view taken in the direction of arrow 4A of FIG. 1A. The macroscopically patterned three-dimensionality imparted to the laminate web 118 is further illustrated in greatly enlarged condition in FIG. 4B, which is a cross-section taken along section line 4B—4B of FIG. 4A. In particular, section line 4B—4B passes through the center of a pair of conical protuberances 120 and 140, simultaneously spanning aperture 169 which defines the base of a downwardly projecting conical protuberance 160 located intermediate protuberances 120 and 140. Upwardly projecting protuberance 130 shown in FIG. 4A has also been illustrated in the cross-section of FIG. 4B to aid in understanding Drawing FIGS. 4A and 4B. As will be appreciated by those skilled in the art, upwardly projecting protuberances such as 120, 130 and 140 correspond to protuberances 213 on male embossing roll 210, while downwardly projecting protuberances such as 160 correspond to protuberances 216 on mating male embossing roll 225.

As can be seen from FIG. 4B, the latex bonded absorbent web 115 remains secured along its uppermost surface 116 to the lowermost surface 114, also referred to as the non-object contacting surface, of the layer of polymeric extrudate 112.

Figure 3:
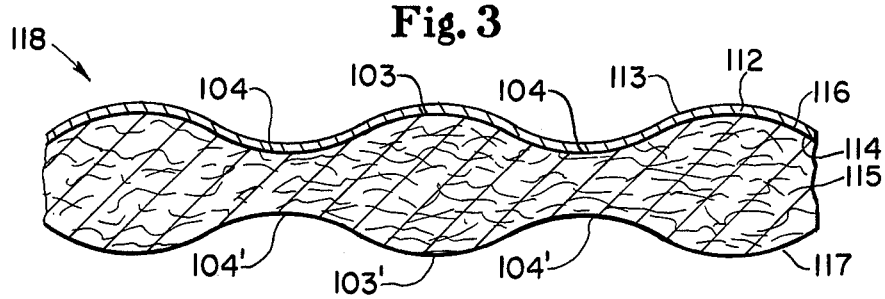
FIG. 3 is an enlarged simplified cross-section taken along section line 3—3 of FIG. 1A showing the web of FIG. 2 after a layer of polymeric film has been extruded onto its uppermost surface and the resultant composite structure passed through the nip between a pair of smooth surfaced compression rolls.
Figure 4A:
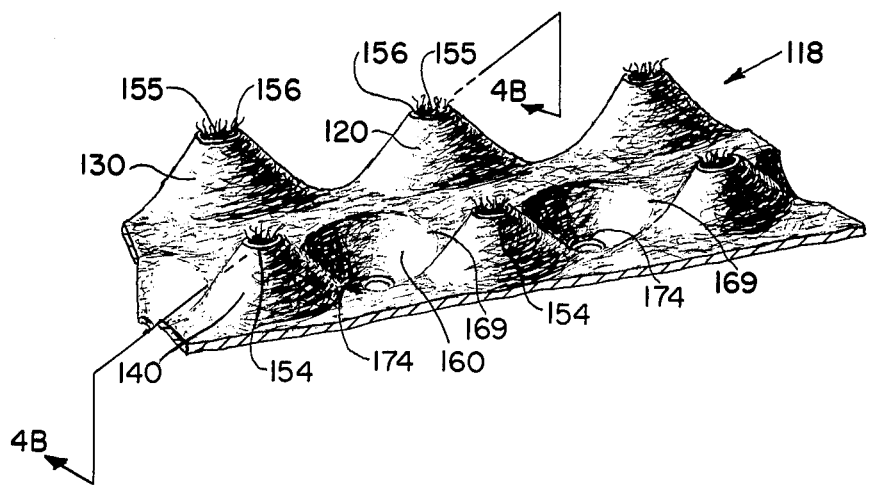
FIG. 4A is a perspective illustration of the laminate web shown in FIG. 3 after the web has been subjected to a three-dimensional embossing process in a roll stack arrangement between a pair of macroscopically patterned, nested, male-to-male embossing rolls as generally shown in FIG. 1A, said view being taken in the direction generally indicated by arrow 4A in FIG. 1A.

As can be seen from FIG. 4A, the laminate web 118 has been three-dimensionally expanded by embossing on a macroscopic scale from the substantially planar condition generally illustrated in FIG. 3. In this regard it should be noted that the scale of enlargement illustrated in FIG. 3 is many times that illustrated in FIG.

4B. Different degrees of enlargement have been utilized in FIGS. 3 and 4B in order to illustrate the fine scale undulating pattern of densified areas 104, 104' present in laminate web 118 prior to its passage through the nip formed between macroscopically patterned embossing rolls 210 and 225. This fine scale undulating pattern of densified areas 104, 104' is still present when the web is in the macroscopically expanded condition illustrated in FIG. 4B, but is so fine in scale relative to the macroscopic pattern of embossment imparted by rolls 210, 225 that it is not readily apparent.

As will be appreciated by those skilled in the art, mating embossing rolls 210 and 225 engage one another at the nip so that the protuberances 213 on roll 210 rest in the valleys 218 of roll 225, while the protuberances 216 on roll 225 rest in the valleys 215 on roll 210. The degree to which rolls 210 and 225 engage one another will depend upon such factors as the overall amplitude of the protuberances 213 and 216 on rolls 210 and 225, respectively, the thickness of laminate web 118 and the degree of macroscopic embossing desired. As can be seen from the macroscopically embossed laminate web 118 shown in FIG. 4B, the intersection between protuberances 213 on embossing roll 210 and protuberances 216 on embossing roll 225 occurs in a plane 125 located approximately midway between the uppermost and lowermost surfaces of the embossed web which terminate in planes 124 and 126, respectively. It is in this plane that discrete apertures 169 are located.

The apertures 155 in the absorbent substrate layer 115 of the three-dimensionally expanded laminate web 118 substantially coincide with the land areas 214 of protuberances 213 on embossing roll 210. This is due primarily to the presence of floating roll 208 which initially causes the laminate web 118 to assume a fixed position relative to said land areas as the web passes through the nip between rolls 208 and 210. The laminate web 118 remains substantially fixed relative to the periphery of embossing roll 210 as its enters the nip formed with mating male embossing roll 225. Because of the anchoring effect provided by the protuberances 213 at their initial points of contact with the absorbent substrate layer 115 of the laminate web 118, three-dimensional expansion of the web is effected by the mating protuberances 216 on embossing roll 225. These mating protuberances 216 on embossing roll 225 contact the uppermost surface 113 of polymeric layer 112 as the laminate web 118 approaches the nip between embossing rolls 210 and 225. Passage through the nip formed by mating male-to-male embossing rolls 210 and 225 causes the web to be deformed from a substantially planar condition into the three-dimensional configuration generally illustrated in FIG. 4B.

The protuberances 216 on the periphery of embossing roll 225 contact the uppermost surface 113 of layer 112 during the three-dimensional embossing cycle, while the protuberances 213 on the periphery of embossing roll 210 contact the lowermost surface 117 of the absorbent substrate layer 115. Because the laminate web 118 is initially fixed in relation to the land areas 214 of adjacent protuberances 213 by virtue of its passage intermediate floating roll 208 and male embossing roll 210, the nesting of protuberances 216 on embossing roll 225 with the corresponding valleys 215 on embossing roll 210 causes the laminate web 118 to undergo three-dimensional expansion intermediate adjacent protuberances 213. The macroscopic pattern of embossment on rolls 210, 225 preferably exhibits an amplitude which will exceed the yield point of the laminate web 118. Accordingly, passage of the web through the nip results in the land areas 217 on protuberances 216 rupturing uppermost layer 112 to form discrete apertures 174 in or near the lowermost plane 126 of the web. In an exemplary embodiment of the present invention formed using conically shaped protuberances 216, apertures 174 exhibited a slightly eliptical shape having a maximum dimension ranging between about 1.0 and about 1.5 millimeters. Depending upon the geometry and amplitude, i.e., the overall height, of the mating protuberances 213 and 216, an aperture 175 may also be formed in absorbent substrate layer 115 immediately beneath aperture 174 in uppermost layer 112, as generally shown in FIG. 4B.

The drawing action which takes place on laminate web 118 during its passage between embossing rolls 210 and 225 also results in the formation of apertures 155 in absorbent substrate 115 and apertures 154 in uppermost layer 112 in or near uppermost plane 124 of the web. In an exemplary embodiment of the present invention formed using conically shaped protuberances 213, apertures 155 exhibited a diameter of approximately 0.5 millimeters, while apertures 154 exhibited a diameter of approximately 1.0 millimeters. These apertures correspond to land areas 214 on protuberances 213 and are formed by the projection of protuberances 213 into the web during the three-dimensional expansion process.

In general, it has been observed that the maximum density of protuberances of a given size which can be provided in a laminate web of the present invention produces the most effective moisture and particulate removal and retention in use. However, beneficial results have been obtained with laminate structures of the present invention wherein protuberance densities as low as 25 percent of the maximum possible are employed. In this regard, it has been observed that as the density of the pattern of protuberances increases, the number of wipes of the soiled object required to obtain satisfactory performance decreases.

It is, of course, recognized that laminate structures of the present invention need not exhibit a continuous pattern of protuberances on their exposed surface to function in their intended manner. For example, artistic designs may be employed wherein protuberances are used in conjunction with planar areas to create an aesthetically pleasing visual appearance or to convey a printed message or logo. Similarly, there is no requirement that all protuberances be identical to one another. For example, patterns of discrete protuberances may be integrated with one or more patterns of ribs and/or planar areas.

Following the three-dimensional embossing operation, the laminate web 118 is removed from the peripheral surface of embossing roll 225. When polymeric materials are employed in the uppermost layer 112 of the laminate web 118, it is generally preferable to subject the macroscopically embossed web to a heat setting operation to dimensionally stabilize the web in its expanded configuration. This may be accomplished by elevating the the temperature of the uppermost layer 112 of the macroscopically expanded web 118 to a temperature approaching its softening temperature. In the illustrated embodiment this is accomplished by means of a hot air heating system comprising inlet conduit 331, distributing hood 332, collection hood 333, and discharge conduit 334. If desired, the hot air exiting discharge conduit 334 may be reheated and continuously recycled by means well known in the art (and therefore not shown) to minimize the energy requirements of the process generally disclosed in FIG. 1A. Alternatively, other conventional heating means such as infrared heat lamps may be employed to obtain similar results.

In a particularly preferred embodiment of the present invention the macroscopically embossed and apertured laminate web 118 exhibits a cross-section of the type generally illustrated in FIG. 4B. The macroscopically embossed and apertured laminate web 118 illustrated in FIG. 4B exhibits a resilient property. When sufficiently large opposing compressive loads are applied, the portions of the web located in planes 124, 125 and 126 are moved closer to one another. However, unless the compressive loads are exceedingly large, i.e., in excess of about 45 pounds per square inch (3.16 kilograms per square centimeter), the portions of the web located in planes 124, 125 and 126 will not become coplanar with one another and the web will generally recover a substantial portion of its initial caliper when the opposing compressive loads are removed.

Figure 13:
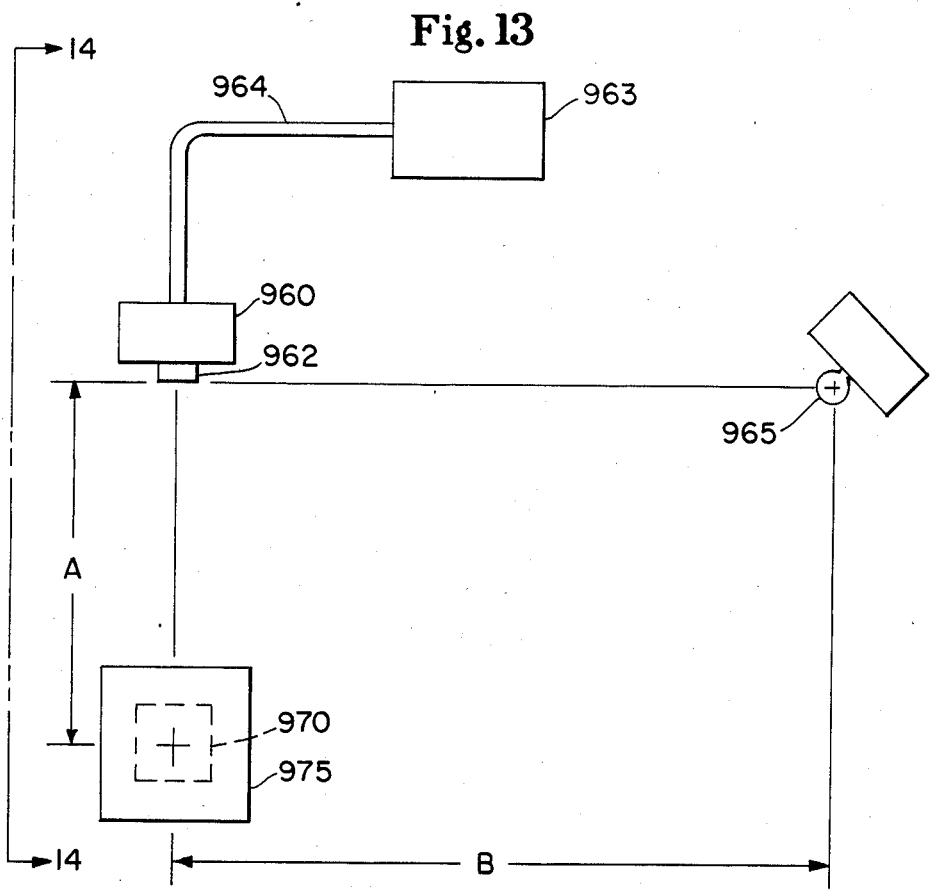
FIG. 13 is a simplified schematic illustration of test apparatus utilized to check a sample structure for the presence of more than a single plane in its uppermost layer when the structure is subjected to predetermined compressive loading.
Figure 14:
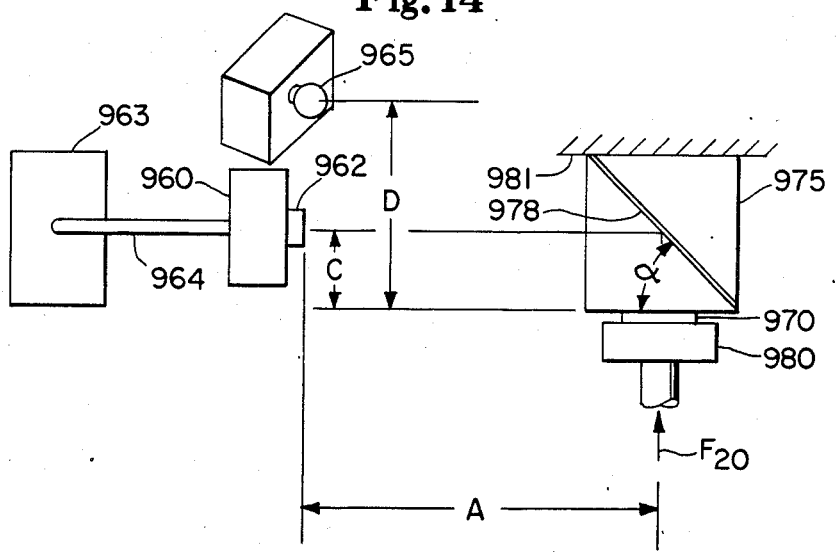
FIG. 14 is a simplified schematic illustration of the apparatus shown in FIG. 13 taken along view line 14—14 of FIG. 13.

Test apparatus for measuring whether or not all portions of a web's uppermost layer become coplanar, as that term is utilized herein, is schematically illustrated in FIGS. 13 and 14.

FIG. 13 is a plan view of the apparatus utilized to make the foregoing measurement showing the relative positions of the various components to one another. A video camera 960, such as a Sony Model DXC1800 available from Sony Corporation of America of New York, N.Y., is preferably equipped with a lens 962, such as a Nikon 135 millimeter Model No. 201632 connected to the camera via a Nikon Model PB-5 Bellows Extension available from Nikon Inc. of Garden City, N.Y. and a c-mount Video Adapter to fit Nikon available from Kalt of Santa Monica, Calif. The camera output is fed via cable 964 to a video monitor 963 such as an 8 inch Videotek Trinitron unit available from Videotek of Pottstown, Pa. The video monitor 963 is utilized to observe whether or not the uppermost layer of a sample being tested enters a single plane as the sample is subjected to a predetermined range of compressive loading. Camera lens 962 is preferably positioned a predetermined distance "A" of 17-$\frac{3}{4}$ inches (45.08 cm.) from the center of a 2 inch (5.08 cm.)×2 inch (5.08 cm.) sample 970 of the particular structure to be tested. A 4 inch 810.16 cm.)×4 inch (10.16 cm.)×4 inch (10.16 cm) cube 975 constructed of translucent $\frac{1}{4}$ inch (0.635 cm.) thick Lucite ® (register trademark of E. I. DuPont de Nemours and Company of Wilmington, Del.) and having a mirror 978 extending at an angle α of 45° from the one corner to a diagonally opposite corner, as generally shown in FIG. 14, is preferably utilized to apply pressure to the material sample 970. The mirror 978 is so positioned inside the translucent box that its reflective surface is oriented toward the material sample 970, as generally shown in FIG. 14. The camera lens 962 is preferably positioned a distance "C" of 2 inches (5.08 cm.) above the uppermost surface of the material sample 970, as generally shown in FIG. 14. For purposes of illumination, a light source 965 such as a Colortram Minipro 600 watt unit with barn doors to aid in directing the light at the sample, available from BMC Inc. of Woodside, N.Y., is preferably positioned a distance "B" of 24 inches (60.96 cm.) to the right of camera lens 962 and a distance "A" of 17-$\frac{3}{4}$ inches (45.08 cm.) from the center of sample 970, as generally shown in FIG. 13. For maximum lighting efficiency, the center of the light source 965 is most preferably positioned a distance "D" of approximately 9$\frac{1}{2}$ inches (24.13 cm.) above the uppermost surface of the sample 970, as generally shown in FIG. 14. The room is preferably darkened and only the light source 965 is used for illumination during the test procedure. The sample structures 970 are preferably rotated through three 90° viewing angles to select the orientation of maximum contrast prior to initiating the compressive loading cycle.

Pressure is applied to the material sample 970 by the lowermost surface of the translucent box 975 and the upwardly moving plunger 980 of a force applicator such as an Instron Model No. 1122 available from Instron Corporation of Canton, Mass. The Instron plunger 980 preferably applies a varying amount of force $F_{20}$, which is opposed by the stationary uppermost portion 981 of the Instron tester. For purposes of the present testing, the Instron tester is preferably utilized to apply a force $F_{20}$ ranging from 0 to 180 pounds (0 to 81.6 kilograms) of a 2 inch (5.08 cm.)×2 inch (5.08 cm.) sample 970 of material. This loading is preferably applied at an upward speed of 2 millimeters per minute, followed by retraction at a downward speed of 2 millimeters per minute.

Samples 970 of the material to be tested are placed in the compression testing apparatus shown in FIGS. 13 and 14 so that their object-contacting surface ultimately contacts the lowermost surface of the translucent box 975. The video camera 960 and lens 962 are preferably adjusted so that a portion of the sample measuring approximately one inch (2.54 cm.) by one inch (2.54 cm.) appears on the total expanse of the 8 inch screen of the video monitor 963.

With three-dimensionally expanded structures of the present invention, the presence of more than a single plane in the uppermost layer of the sample 970 is reflected by the presence of more than a single color or shade on the video monitor. With sample embodiments of the present invention, application of a force $F_{20}$ varying from 0 to 180 pounds (0 to 81.6 kilograms) to the 2 inch (5.08 cm.)×2 inch (5.08 cm.) samples 970 did not force the uppermost layer of the samples into a single plane, as would be reflected by the presence of only a single color or shade on the video monitor. This translates to an applied pressure of 45 pounds per square inch (3.16 kilograms per square centimeter). In fact, exemplary embodiments of the present invention at all times during the pressure loading cycle exhibited the presence of two colors or shades, thus reflecting the presence of more than a single plane in the uppermost layer of the sample structure being tested. It was further observed that as the compressive loading of the sample was increased, the proportion of one color or shade to the other underwent change, but at no time during the 0 to 180 pound (0 to 8.16 kilogram) test cycle was the second color or shade completely eliminated. Thus, one distinguishing characteristic of structures of the present invention is that they exhibit more than a single color or shade when subjected to the aforementioned test procedure at compressive loads of up to about 45 pounds per square inch. By way of contrast, samples of similarly constructed unembossed materials were placed in the position shown in FIGS. 13 and 14 and cycled through an identical test. These particular samples illustrated the presence of only a single color or shade throughout the entire range of compressive loading, thus demonstrating the existence of only a single plane in their uppermost layer.

interestingly, samples of the present invention were found to exhibit enough resistance to compression, even when wetted with a quantity of water having a weight equal to that of the aborbent substrate, to avoid becoming coplanar when subjected to compressive loading in the aforementioned manner at pressures of up to 45 pounds per square inch (3.16 kilograms per square centimeter).

The wetted samples are preferably prepared by immersing them in water, manually shaking them upon removal and thereafter contacting only the object-contacting surface of the sample with a paper towel to remove any free-standing droplets of moisture present on the uppermost layer prior to placing them on the Instron compression tester. It is believed that the foregoing resistance to compression exhibited by structures of the present invention in both the wet and the dry state provides improved retention of particulate soil regardless of the nature of the environment in which the mat is employed, i.e., wet, dry or a combination thereof.

While the uppermost layer of the samples tested were of uniform white color, the present test may be applied with equal facility to structures employing multicolors or printed patterns on their uppermost layers. This is accomplished by spraying a light coat of white spray paint, such as Effecto Spray Enamel White Gloss Paint No. E850 available from Pratt & Lambert of Buffalo, N.Y. on the uppermost surface of the structure prior to initiating the test. This painting procedure has been found particularly helpful when the samples being tested are wetted with water rather than dry.

As shown in FIG. 4B, the apertures 155 present in absorbent substrate layer 115 are each bounded by a circular fibrous tuft 156 which projects slightly above the corresponding aperture 154 formed in uppermost layer 112. These projecting fibrous tufts 156 have been found to function in several important regards when laminate webs 118 of the present invention are utilized either directly in the form generally illustrated in FIG. 4B or when additional structural elements are added to meet specific use requirements. When combined with the overall resilience characteristic of three-dimensionally expanded laminate webs of the present invention, the circular fibrous tufts 156 tend to act as fine brushes which serve to dislodge particulate soil from a soiled object coming in contact with the object contacting surface 113 of uppermost layer 112. Because of the presence of the substantially concentric apertures 154 and 155 in layers 112 and 115, respectively, particulate soil encompassed within each of the fibrous tufts 156 and removed from the soiled object by abrasion can pass through and/or become entangled within absorbent substrate layer 115. In either event, dislodged soil passing through apertures 154 becomes physically isolated from the object being cleaned by uppermost layer 112.

When the laminate web 118 is oriented as generally shown in FIG. 4B, the apertures 174 in uppermost layer 112 near lowermost plane 126 provide a gravity assisted collection and entry point for particulate soil which is not encompassed by circular fibrous tufts 156 when initial contact with the soiled object is made, but which is dislodged by the abrasion imparted by the fibrous tufts. In addition, apertures 174 in layer 112 permit volumes of moisture too large to be handled by apertures 154, 155 to rapidly reach absorbent layer 115. Where, as shown in FIG. 4B, complete aperturing of absorbent substrate layer 115 is provided in plane 126, particulate soil reaching apertures 175 is free to pass through and/or become entangled with absorbent substrate layer 115. In those instances where only the uppermost layer 112 has been ruptured to produce apertures 174, a portion of the absorbent substrate layer 115 is directly exposed to both moisture and particulate soil transferred from the object. In the latter case, particulate soil dislodged outside circular fibrous tufts 156 is allowed to roll down the outermost surfaces of the upwardly extending conical protuberances, e.g., protuberances 120, 130 and 140, pass through discrete apertures 169 located intermediate said upwardly extending protuberances in the first plane of uppermost layer 112, continue down the innermost surfaces of the downwardly extending protuberances, e.g., protuberance 160, and ultimately enter into and become entangled with those portions of absorbent substrate layer 115 which are present in the generally vicinity of apertures 174.

Another beneficial function performed by circular fibrous tufts 156 in plane 124 is rapid wicking of moisture from the soiled object into the absorbent substrate layer 115 which is continuously secured to the lowermost surface 114 of uppermost layer 112.

When the volumes of moisture involved are too large to be instantaneously and completely handled by direct entry via apertures 154 and/or by the wicking action provided by fibrous tufts 156, apertures 174 in layer 112 provide secondary points of entry into absorbent substrate layer 115 for excess moisture deposited on the uppermost surface 113 of layer 112.

In a particularly preferred embodiment of the present invention uppermost layer 112 is substantially impervious to both moisture and particulate at points other than apertures 154 and 174. Accordingly, soils absorbed and/or entangled within layer 115 are effectively isolated from objects coming in contact with uppermost surface 113 of layer 112. This substantially prevents redeposition of either moisture or particulate transferred from a soiled object and into absorbent substrate layer 115 back onto the object.

While moisture-impervious polymeric materials such as continuous extrudates and/or continuous films represent preferred materials of construction for uppermost layer 112 in a process such as that disclosed in FIGS. 1A and 1B, it is recognized that the present invention could also be practiced to advantage using an uppermost layer comprised of a moisture-pervious material, such as a non-woven. In the event such a material were employed as uppermost layer 112, a processing operation generally similar to that disclosed in FIG. 1A could be utilized. However, as is the case when a continuous web of polymeric film is utilized in lieu of an extrudate, application of a bonding adhesive to join the non-woven web to absorbent substrate layer 115 would likely be required.

Furthermore, there would be a significant difference in the way moisture deposited on uppermost layer 112 enters absorbent substrate layer 115 of the resultant laminate web. In particular, the moisture-pervious nature of uppermost layer 112 would permit moisture which fails to directly enter absorbent substrate layer 115 via discrete apertures 154 in uppermost layer 112 to enter the absorbent substrate layer 115 at any point along the surface of layer 112 without need for any additional discrete apertures. Thus a moisture and particulate removal and retention structure of the present invention could, if desired, be constructed with discrete apertures in only its uppermost plane 124. Although not entrapped within the absorbent substrate layer 115, particulate soil collected intermediate adjacent upwardly extending protuberances would be effectively isolated from objects coming in contact with the structure so long as the portions of the uppermost layer initially in the first and second planes of the web do not become coplanar with one another under load.

Because of their desirable moisture and particulate removal and retention qualities, three-dimensionally expanded laminate webs of the present invention, such as embodiment 118 shown in the cross-section of FIG. 4B, may be utilized to advantage without the addition of further structural elements for applications such as disposable cleansing and/or polishing implements. By way of non-limiting example, a disposable scrub mitt could be fabricated so that its object contacting surface corresponds to surface 113 of layer 112. If polishing is the end objective, the mitt could be fabricated so that lowermost surface 117 of absorbent substrate 115 is the object contacting surface. The mitt could also be fabricated so that opposite sides of the web 118 were exposed on opposite surfaces of the mitt. This would permit one surface to be used for scrubbing and the other for polishing. Other uses of such three-dimensionally expanded laminate webs will be readily apparent to those skilled in the art.

Figure 9:
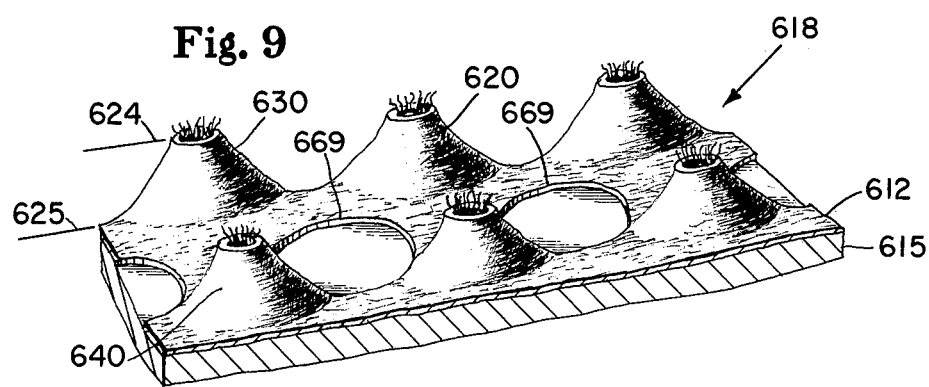
FIG. 9 is an enlarged perspective illustration of an embodiment of a laminate web of the present invention which is generally similar to the embodiment shown in FIG. 4A, but which does not employ downwardly extending protuberances in its uppermost layer.

FIG. 9 discloses an alternative embodiment of a macroscopically patterned, three-dimensionally expanded laminate web structure 618 of the present invention. The laminate web 618 comprises an absorbent substrate 615 similar to layer 115 of web 118 and an uppermost layer 612 similar to layer 112 of web 118. Protuberances 620, 630, and 640 of laminate web 618 correspond to protuberances 120, 130 and 140 of laminate web 118. Apertures 669 in lowermost plane 625 correspond to apertures 169 in plane 125 of laminate web 118. The chief distinction between the web embodiment 618 disclosed in FIG. 9 and the web embodiment 118 disclosed in FIG. 4A is that web embodiment 618 does not employ any downwardly extending protuberances corresponding to protuberance 160 in web 118. Accordingly, soils collecting at or near aperture 669 in layer 612 enter absorbent substate layer 615 directly. As with laminate web embodiment 118, those portions of uppermost layer 612 initially located in uppermost plane 624 do not become coplanar with those portions of uppermost layer 612 initially located in lowermost plane 625 when the web 618 is subjected to normal compressive loading.

Figure 10:
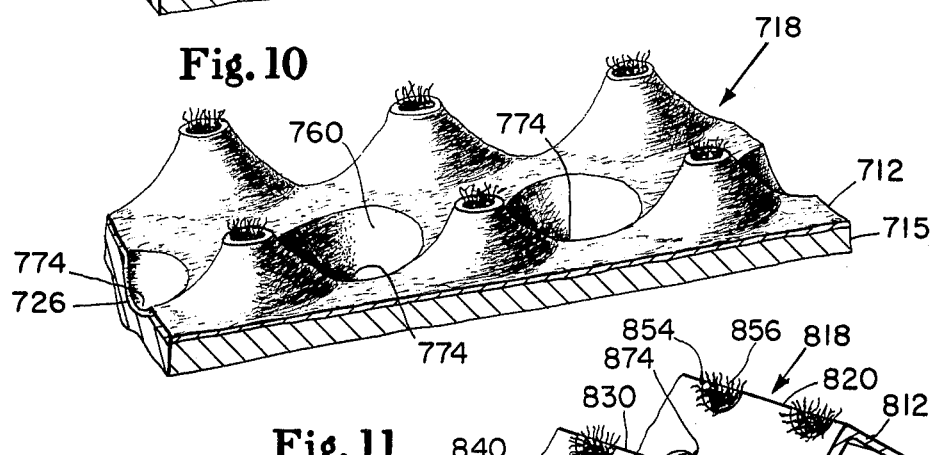
FIG. 10 is an enlarged perspective illustration of an embodiment of a laminate web of the present invention, said web being generally similar to the embodiment disclosed in FIG. 4A, but employing an uppermost layer comprised of moisture-pervious material and having no discrete apertures at the terminal end of its downwardly extending protuberances.

FIG. 10 discloses another embodiment 718 of a laminate web of the present invention which is generally similar to embodiment 118 shown in FIG. 4A. The primary difference is that the uppermost or object contacting layer 712 is comprised of moisture-pervious material rather than moisture-impervious material. In addition, since uppermost layer 712 is comprised of moisture-pervious material, it is not a requirement that discrete apertures be provided in those portions of layer 712 which are located in lowermost plane 726 in order for moisture to enter into absorbent substrate layer 715. This is particularly true where it is anticipated that the structure's primary utility will be in wet soil environments, e.g., bath rooms. Accordingly, the terminal ends 774 of the downwardly extending protuberances, e.g., protuberance 760, of web 718 may, if desired, be comprised of the moisture-pervious material of layer 712.

Figure 11:
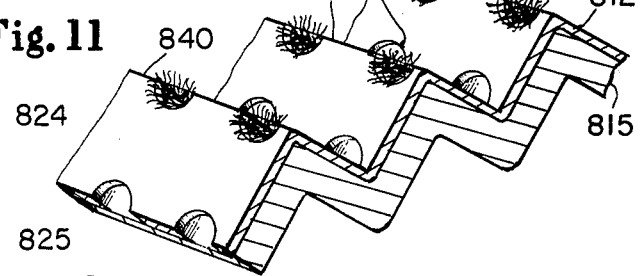
FIG. 11 is an enlarged perspective illustration of another embodiment of a laminate web of the present invention wherein the upwardly extending protuberances comprise a multiplicity of substantially parallel, longitudinally extending ribs.

FIG. 11 discloses another laminate web embodiment 818 of the present invention wherein the upwardly extending protuberances, e.g., protuberances 820, 830 and 840, comprise a multiplicity of substantially parallel, longitudinally extending ribs. Uppermost layer 812 corresponds substantially to uppermost layer 112 of web 118, while absorbent substrate layer 815 corresponds substantially to absorbent substrate layer 115 of laminate web 118. A multiplicity of discrete apertures 854 are provided in uppermost plane 824 at the peaks of the ribs in uppermost layer 812. Circular fibrous tufts 856 project slightly above apertures 854. A multiplicity of discrete apertures 874 is also provided in lowermost plane 825 in the valleys intermediate the adjacent longitudinally extending protuberances.

Figure 12:
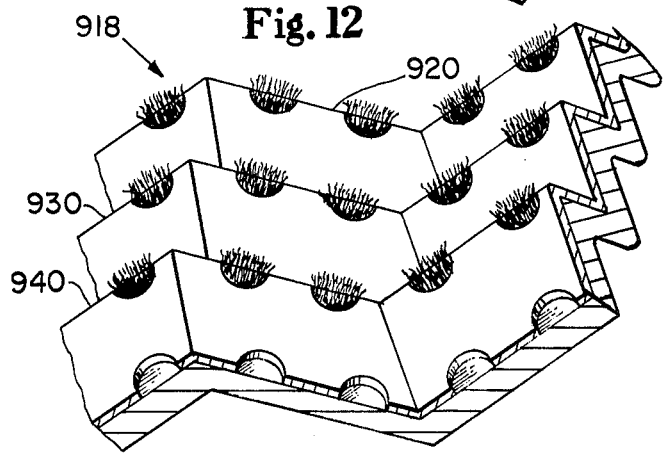
FIG. 12 is an enlarged perspective illustration of still another embodiment of a laminate web of the present invention, said web being generally similar to the embodiment illustrated in FIG. 11, but having the longitudinally extending ribs propagating across the web's surface in a chevron-like pattern.

FIG. 12 discloses still another embodiment 918 of a laminate web of the present invention. Laminate web embodiment 918 is generally similar to embodiment 818 shown in FIG. 11, except that the longitudinally extending protuberances, e.g., ribs 920, 930 and 940 are arranged in a chevron-like pattern across the surface of the web.

In the particularly preferred embodiment of the present invention disclosed in FIGS. 1A and 1B, the macroscopically embossed laminate web 118 shown in FIG. 4B is further processed generally in accordance with the system disclosed in FIG. 1B to provide a low cost, disposable absorbent floor mat which will function well to remove and retain both moisture and particulate from soiled objects coming in contact therewith.

This preferably involves the addition of a moisture-impervious barrier layer 236 comprised of a material such as polymeric film 236 to the lowermost surface 117 of absorbent substrate 115. A particularly preferred material for layer 236 comprises a layer of 0.6 mil (0.0006 inch) thick Nylon Capron 77C, such as is available from the Allied Chemical Company of Morristown, N.J. In the embodiment illustrated in FIG. 1B, the polymeric film barrier layer 236, which may for example be polyethylene, is first coated on its lowermost surface with an adhesive 255 by means of a pair of metering rolls 240, 242 and a doctor blade 241 operating in conjunction with an adhesive reservoir 250. A substantially uniform coating of adhesive is preferably applied to the lowermost surface of the film. A particularly preferred adhesive 255 comprises an acrylic emulsion such as Richadh Adhesive Code 294 available from the E. R. Carpenter Company of Richmond, Va.

The lowermost surface of the film 236 is thereafter introduced into a nip between a pair of smooth surfaced compression rolls 260, 262 where a predetermined force $F_5$ is applied to floating roll 260 to securely bond the polymeric film layer 236 to the uppermost surface 258 of a web of a resilient material 257 such as open celled polyurethane foam. The resultant film/foam laminate is thereafter passed to a secondary metering station where another adhesive 267 is preferably applied to the uppermost surface of film 236 by means of metering rolls 271, 273 and doctor blade 269 operating in conjunction with adhesive reservoir 265. The adhesive 267 may be applied as a continuous layer or in a printed pattern, provided the adhesive coverage is sufficient to prevent layer separation when the mat is subjected to shear stress caused by wiping and twisting in use. In a particularly preferred embodiment of the present invention, adhesive 267 comprises Thixon 951 aqueous polymer emulsion such as is available from the Whittaker Chemical Company of West Alexandria, Ohio. In general, the greater the area of adhesive coverage, the greater will be the shear resistant strength and integrity of the resultant floor mat structure. The laminate structure comprising adhesive coated layer 236 and resilient layer 257 is thereafter fed into a nip between smooth surfaced combining rolls 230, 235 along with the macroscopically patterned, three-dimensionally expanded laminate web 118.

In an alternative embodiment of the present invention, adhesive coated layer 236 could, if desired, be elininated altogether and resilient layer 257 bonded directly to lowermost surface 117 of absorbent substrate layer 115 by means of a continuous layer of hot melt adhesive which also functions as a moisture barrier layer.

The smooth surfaced roll 230 shown in FIG. 1B is a floating roll and the amount of force $F_6$ applied thereto may be adjusted to provide the desired degree of contact between lowermost surface 117 of absorbent substrate layer 115 and the adhesive coated uppermost surface of film layer 236.

As a result of the foregoing combining step, a multilayer composite structure 119 such as that shown in the cross-section of FIG. 5 results. In particular, bonding of the film/foam laminate to the lowermost surface 117 of absorbent substrate 115 is carried out by causing a substantial degree of temporary deformation of the three-dimensionally expanded laminate 118 as the two webs pass through the nip formed between smooth surfaced rolls 230 and 235. The adhesive 267 on the uppermost surface of moisture-impervious layer 236 adheres to the lowermost surface 117 of the absorbent substrate layer 115 in those areas where contact is made.

Once these surfaces have contacted one another, a bond forms between absorbent substrate layer 115 and the adhesive coated portions of the uppermost surface of moisture-impervious layer 236. Thus, when the resultant laminate structure 119 passes out of the nip between rolls 230 and 235, the absorbent substrate 115 is subject to a degree of internal stress. This is caused by the tendency of the resilient three-dimensionally expanded laminate web 118 to return to the condition existing prior to the combining step, i.e., the amplitude shown in FIG. 4B. Because a substantial portion of the lowermost surface 117 of absorbent substrate layer 115 is at this point bonded to the uppermost surface of moisture barrier layer 236, this tendency is to a degree resisted. As a result, the stresses which are exerted substantially perpendicular to the surface of the moisture barrier 236 in the areas where adhesive 267 is present cause a degree of fiber separation within the absorbent substrate layer 115 intermediate its uppermost surface 116 and its lowermost surface 117. If, as shown in FIG. 5, adhesive 267 is present in a uniform layer, the degree of fiber separation is greatest at or near apertures 155, since these areas coincide with the maximum initial amplitude between moisture-impervious barrier layer 236 and the uppermost surface 113 of layer 112 prior to passage of laminate web 118 through the nip between rolls 230 and 235. Consequently the greatest degree of fiber separation occurs in the vicinity of apertures 155, and decreases steadily in the direction of apertures 174, where there is little change in overall amplitude as a result of combining laminate web 118 with the film/foam laminate comprising layers 236 and 257.

The moisture-impervious layer 236 performs two important functions when utilized in a disposable absorbent floor mat structure. First, it provides a moisture barrier to prevent moisture introduced into absorbent substrate 115 from reaching the floor on which the mat structure is ultimately placed. Second, the moisture barrier layer 236, by virtue of its bonding to both foam layer 257 and a substantial portion of the lowermost surface 117 of absorbent substrate 115, imparts integrity as well as shear and compression resistance to the mat structure in use. It is this integrity which prevents separation of the layers of the composite structure from one another when the uppermost surface 113 of layer 112 is subjected to a wiping or scrubbing action such as typically occurs to remove moisture and particulate from soiled shoes while the floor contacting surface of the mat remains stationary. Furthermore, the bonding of layer 236 to the lowermost surface 117 of absorbent substrate 155 prevents shifting of laminate web 118 at its points of contact with layer 236 when the entire structure is subjected to compressive loading. This, in turn, increases the uppermost layer's resistance to becoming coplanar under compressive loading.

As will be clear from a comparison of FIG. 5 with FIG. 4B, the distance of separation or amplitude between the uppermost and lowermost surfaces of the two layer laminate web 118 shown in FIG. 4B, i.e., the distance between planes 124 and 126, has been reduced somewhat due to both the calendering effect which results from passage of the web between combining rolls 230 and 235 and the restraining effect imposed by bonding of the lowermost surface 117 of absorbent substrate layer 115 to a substantial portion of the uppermost surface of moisture barrier layer 236.

The resilient layer 257 which is preferably secured by means of adhesive 267 to the lowermost surface of moisture barrier layer 236 imparts resilience to the mat structure to provide better conformance of the mat to the soles and heels of the wearer's shoes or to the surfaces of other moist and/or soiled objects coming in contact therewith in use. Accordingly, it is desired that layer 257 be reasonably resilient, yet not undergo complete collapse when subject to in use pressures corresponding to those typically applied by human foot traffic. So long as resilient layer 257 does not undergo complete collapse, the compressive forces exerted by human traffic are normally insufficient to cause those portions of uppermost layer 112 normally located in uppermost plane 124 to become coplanar with those portions of layer 112 initially located either in first plane 125 or third plane 126, thereby avoiding redeposition of the loosened soils onto the object. The visual test method employed to check for coplanarity of the uppermost layer of any given sample under compressive loading is recited in detail earlier herein. Although a maximum test pressure of up to 45 pounds per square inch (3.16 kilograms per square centimeter) is employed in the aforementioned test, experience has demonstrated that normal standing pressures caused by human traffic are typically in the range of from about four to about five pounds per square inch (about 0.28 to about 0.35 kilograms per square centimeter). For example, a 300 lb. man wearing a size 7½ shoe and standing on one foot without the shoe arch touching the ground would exert an estimated loading of 13.4 pounds pr square inch (0.942 kilograms per square centimeter), assuming a 60 percent shoe contact area. For a size 11 shoe, the estimated loading would drop to 7.3 pounds per square inch (0.513 kilograms per square centimeter). For a 400 lb. man under similar circumstances, a size 7½ shoe would result in an estimated loading of 17.9 pounds per square inch (1.26 kilograms per square centimeter), while a size 11 shoe would result in an estimated loading of 9.7 pounds per square inch (0.682 kilograms per square centimeter).

The resilient layer 257 also provides a secondary benefit in that it offers a degree of curl resistance to the mat to prevent extensive curling or rolling up when a scrubbing action is imparted to the uppermost surface of the mat.

In a particularly preferred embodiment, the resilient layer 257 comprises an open celled, resilient polyurethane foam. The open celled structure provides a degree of roughness on the lowermost surface 259 of layer 257. The roughness provided by the open celled structure permits a degree of entangling with the fibers present on carpeted surfaces. This entanglement imparts floor stability and skid resistance to the floor mat when used on carpeted surfaces.

To ensure that the mat structure can be utilized with equal facility on either hard surfaced or carpeted floors, a coating operation which applies a very small quantity of skid resistant, pressure sensitive adhesive 282 to the exposed lowermost surface 259 of the resilient layer 257 is preferably carried out. In a particularly preferred embodiment of the present invention, pressure sensitive adhesive 289 comprises Hycar 2600×20C Acrylic latex containing Carboset XL46 Acrylic resin stabilizer, both of said materials being available from the B. F. Goodrich Company of Cleveland, Ohio. In the embodiment illustrated in FIG. 1B, this is done by means of a pair of metering rolls 284 and 285 operating in conjunction with a doctor blade 283 and an adhesive reservoir 280. A backup roll 286 is preferably employed opposite metering roll 285. A fixed nip distance is preferably employed between rolls 285 and 286 so that the multi-layer laminate 119 undergoes little or not deformation as a thin layer of pressure sensitive adhesive 282 is applied to only the lowermost points 289 of the rough lowermost surface 259 which typically inheres in material such as open celled polyurethane foam. The results of the foregoing operation are best illustrated in the cross-section of FIG. 6.

The spots of pressure sensitive adhesive 289 provide sufficient tack of the mat structure to a hard surfaced floor that the mat does not readily slide or move when shear stresses are applied to its uppermost surface, yet the quantity of adhesive present is not so great that the mat becomes difficult to remove when it is intentionally picked up from overhead, as by peeling. In addition, the pressure sensitive adhesive 289 aids in securing the roughened surface 259 of resilient layer 257 to carpeted surfaces by securing carpet fibers thereto. This in turn helps to prevent curling of the edges of the mat in use.

While pressure sensitive adhesives represent a preferred means for imparting a suitable degree of skid resistance to disposable floor mats of the present invention, other means known in the art may be used with equal facility, e.g., double sided adhesive tapes, permanently anchored retaining structures and the like.

While nearly any resilient material can be utilized for the layer 257, it has been found that Polyurethane Foam L-45, such as is available from E. R. Carpenter Company of Richmond, Va. functions particularly well in this regard. The thickness of the resilient layer 257 is preferably within the range of about 1/16 inch (1.6 mm.) to about ½ inch (12.7 mm.), most preferably between about 1/16 inch (1.6 mm.) and about ¼ inch (6.4 mm.).

Following the application of pressure sensitive adhesive 289, the uppermost surface 113 of uppermost layer 112 may, if desired, be subjected to a treatment designed to impart hydrophilicity thereto. In the embodiment illustrated in FIG. 1B, this may be accomplished by spraying a hydrophilic coating 295 comprised of a material such as a 0.01 percent aqueous solution of colloidal silica onto the uppermost surface 113 of layer 112 by means of spray nozzle 290 as the web 119 passes below. In a particularly preferred embodiment of the present invention, the colloidal silica comprises Wesol P Alumina coated colloidal silica available from the Wesolite Company of Wilmington, Del., said silica including a 0.01 percent binder such as Parez 631NC available from the American Cyanimide Company of Wayne, N.J. Suitable substances for forming such coatings include materials such as solutions of colloidal silica clays, surfactants and the like.

Alternatively, where layer 112 comprises a polymeric film such as polyethylene, well known surface treatments such as corona discharge may be applied to the uppermost surface 113 to alter the contact angle made by liquids which come in contact therewith and thereby facilitate more rapid transport of the liquids deposited on surface 113 into absorbent substrate 115 through apertures 155 and 174. These surface treatments may be performed by any of numerous means well known in the art.

In the event a coating of liquid material 295 is employed to impart the desired properties to uppermost surface 113 of layer 112, the coating is preferably dried by applying hot air to the web. In the embodiment illustrated in FIG. 1B, air in a heated condition is introduced to distributor head 305 through inlet conduit 300, applied across the width of the web by distributor means well known in the art. Alternatively, drying can be carried out by other conventional means such as infrared heat lamps.

While the laminate mat structure 119 illustrated in FIG. 6 may, if desired, be wound into rolls and cut into any desired shape by the end user, the system illustrated in FIG. 1B includes rotary cutting means comprising a rotating cylinder 320 having a pair of blades 325 and 330 mounted diametrically opposed from one another. A hard surfaced backup roll 340 is employed beneath the moving composite web 119. The knives 325 and 330 cut the moving web 119 into discrete floor mats 410 of predetermined dimension, as generally shown in FIG. 1B. The finished mats 410, which represent a particularly preferred embodiment of the present invention, exhibit a cross-section of the type generally disclosed in FIG. 6. The discrete floor mats 410 are at this point ready for use by the consumer.

Figure 7:
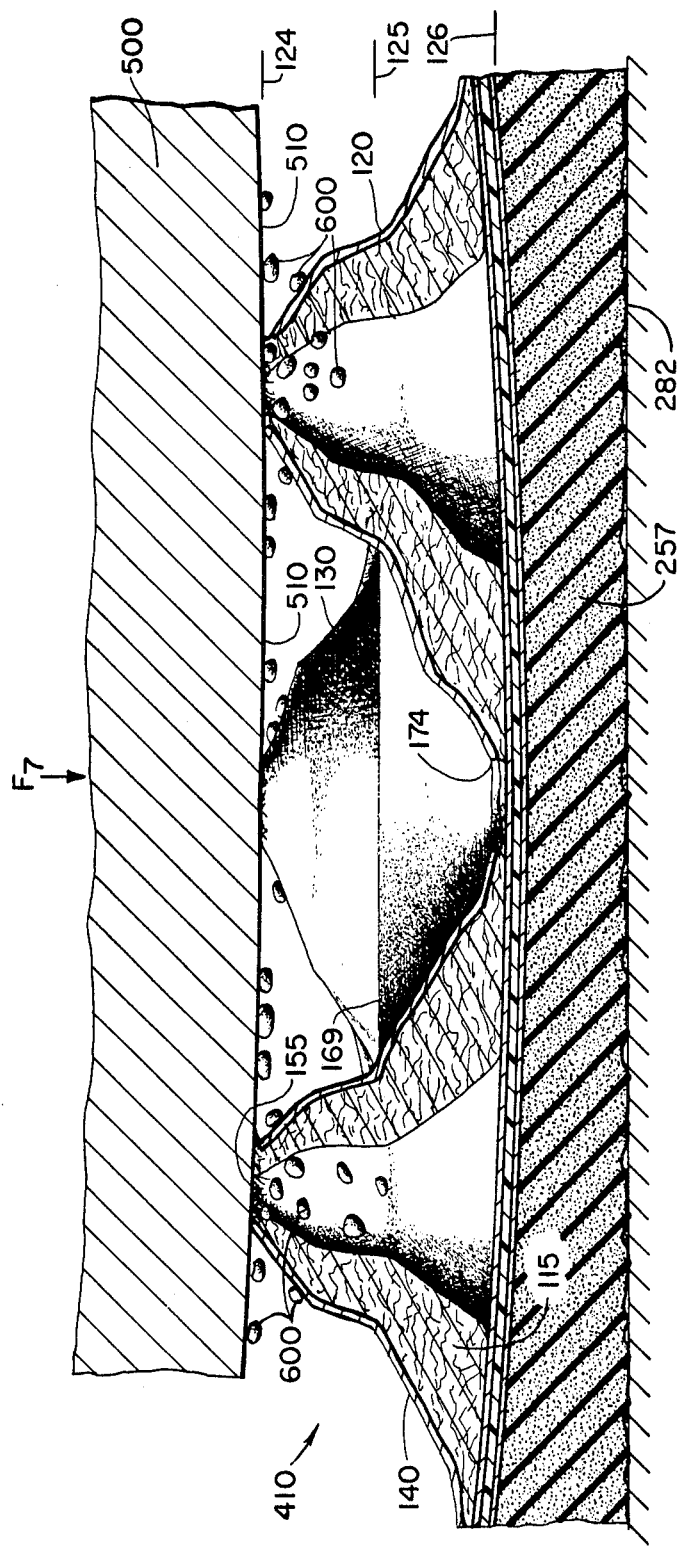
FIG. 7 is a greatly enlarged simplified cross-section of a floor mat of the type generally shown in FIG. 6 illustrating the deformation which takes place during the transfer of soils from a soiled object to the mat structure under normal use conditions.

FIG. 7 discloses the condition of such a floor mat 410 when a soiled object such as a shoe sole 500 comes in contact with its uppermost surface. In particular, the resilient layer 257 permits deformation so as to maximize the area of contact between the uppermost surface of the mat and the bottom of the wearer's shoe. As can be seen in the greatly enlarged cross-section of FIG. 7, particulate soil 600 clinging to the bottom of the shoe sole tends to become dislodged by virtue of the contact with circular fibrous tufts 156 projecting through the apertures 154 in uppermost layer 112. As can also be seen in FIG. 7, much of the particulate soil 600, particularly that encompassed by the circular tufts 156 upon initial contact, enters directly through apertures 154 into absorbent substrate layer 115 where it becomes entangled and retained.

In the event a scrubbing or twisting action, i.e., relative movement, is effected between the bottom 510 of the sole 500 and the circular fibrous tufts 156, particulate soil 600 is scrubbed from the bottom of the sole and either enters the absorbent substrate 115 through apertures 154 or collects at or near apertures 174 intermediate adjacent protuberances, e.g., protuberances 120, 130 and 140. In this regard, it is significant to note that although the plane in which apertures 154 are located, i.e., uppermost plane 124, the plane in which apertures 169 are located, i.e., plane 125, and the plane in which lowermost apertures 174 are located, i.e., lowermost plane 126, have moved closer toward one another when a typical compressive load, i.e., (a load which is not in excess of 45 pounds per square inch (3.16 kilograms per square centimeter), is applied to the uppermost surface of the mat, they do not become coplanar. Hence redeposition of the soil on the shoe sole is substantially avoided.

Figure 8:
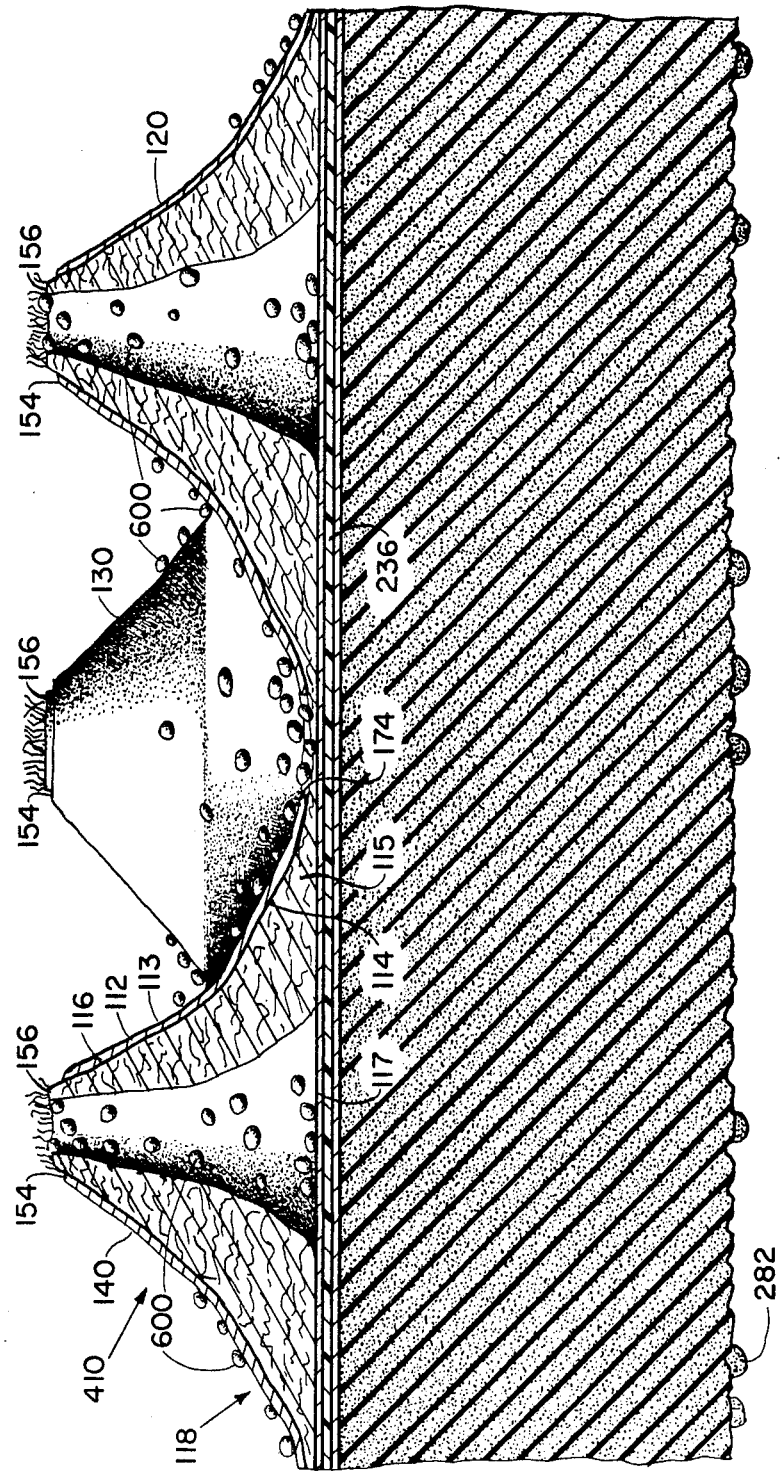
FIG. 8 is a cross-section of the mat structure shown in FIG. 7 after the soiled object shown in FIG. 7 has been removed therefrom.

Furthermore, the floor mat structure 410 exhibits a substantial recovery toward its original condition when the compressive load $F_7$ applied by the shoe sole 500 is removed from the surface of the mat. This is best illustrated in FIG. 8, which exhibits the manner in which particulate soil 600 initially introduced into absorbent substrate layer 115 through apertures 154 in layer 112 tends to further penetrate into the relatively open areas immediately below the apertures during the resilient recovery phase. Particulate soil deposited outside the circular fibrous tufts 156 and intermediate adjacent upwardly extending protuberances, e.g., protuberances 120, 130 tends to roll down and collect in the downwardly extending protuberances, e.g., protuberance 160, from whence it is ultimately free to enter absorbent substrate layer 115. This resilience property is readily observable as a return toward the original color or shade contrast when the maximum compressive load is removed from sample structures of the present invention at a predetermined rate during conduct of the coplanarity test is described earlier herein.

Resilient recovery of the floor mat structure 410 in the direction of its original amplitude upon removal of the compressive load is, to a degree, repeated with each compressive loading cycle. This, in turn, promotes further penetration of particulate 600 into absorbent substrate layer 115 where it becomes entangled and retained.

As can be seen from the typical in use cross-section of FIG. 7, even under a normally loaded condition, apertures 154 located in or near plane 124, apertures 169 located in plane 125 and apertures 174 located in or near plane 126 never become completely coplanar. This means that once particulate soil 600 has been removed from the bottom 510 of shoe sole 500, the loosened soil is physically separated from the bottom of the shoe sole. It either enters absorbent layer 115 directly through apertures 154 in uppermost layer 112 or collects at or near apertures 174 from whence it is ultimately free to enter absorbent layer 115 over a number of use cycles. As a minimum, it remains physically separated from the bottom or lowermost surface 510 of the shoe sole 500. In the event it enters absorbent layer 115 through apertures 174, it becomes physically isolated from the shoe sole 500 by means of uppermost object contacting layer 112. These phenomena both minimize redeposition and consequent tracking of particulate from the surface of the floor mat after the soil has been initially removed from the shoe sole or other object being cleaned.

Multiple recovery cycles which the floor mat undergoes in use cause the floor mat to cycle from the condition generally illustrated in FIG. 7 to the condition generally illustrated in FIG. 8, each cycle causing deposited particulate 600 to work its way further into the absorbent substrate 115 until the void volume of the mat, i.e., the unoccupied volume within absorbent substrate layer 115 per se as well as the unoccupied void volume created between uppermost layer 112 and moisture barrier layer 236, has been substantially filled with soil.

The aforementioned penetration of the floor mat 410 by the particulate 600 with each use cycle tends to keep the mat from developing an unsightly appearance long before its void volume has been substantially utilized. In addition it serves to physically contain the soils and thereby helps to prevent loss of the mat's soil load when it is finally picked up for disposal.

As has been pointed out earlier herein, floor mat structures 410 of the present invention are designed to absorb and retain moisture as well as to entrap and retain particulate soil. While prior art structures have typically been unable to effectively handle both wet and dry soils, moisture transferred into absorbent substrate 115 of floor mat 410 by means of apertures 154 and apertures 174 serves not only to cleanse the uppermost surface 113 of layer 112, but also to wash the particulate 600 deeper into the absorbent substrate 115.

This is another reason disposable absorbent floor mats 410 of the present invention are less prone to prematurely develop on objectionable appearance before their soil loading capacity has been fully and effectively utilized. When the moisture absorption and/or the particulate retention capacity of the floor mat 410 have been exhausted, the loaded structure can be easily removed from the surface which it protects with the bulk of the moisture and particulate soil being trapped intermediate the confines of uppermost layer 112 and moisture barrier layer 236. In this regard it is recognized that absorbed moisture typically evaporates intermediate use cycles, provided the duration of time intermediate use cycles is sufficiently long. Hence the life of a disposable absorbent mat 410 of the present invention is typically much longer when it is used in environments limited primarily to wet soils, e.g., as a bath mat, a place mat, a drip mat for use under automobiles or the like.

While particular embodiments of the present invention have been illustrated and described, it will be obvious to those skilled in the art that various changes and modifications can be made without departing from the spirit and scope of the invention. It is intended to cover in the appended claims all such modifications that are within the scope of this invention.

What is claimed is:

1. A disposable absorbent structure for removal and retention of moisture and particulate from a soiled object coming in contact therewith, said structure comprising:

(a) a macroscopically patterned, three-dimensionally expanded, shear-resistant uppermost layer having an object contacting surface and a non-object contacting surface, said uppermost layer exhibiting a pattern of protuberances originating in and extending upwardly from a first plane and terminating in a second plane substantially parallel to and remote from said first plane, said uppermost layer being pervious to moisture in said first plane intermediate adjacent protuberances, said uppermost layer further exhibiting a multiplicity of discrete apertures in said second plane, said apertures in said second plane being located at the terminal end of said protuberances originating in said first plane; and (b) a moisture absorbent substrate having its uppermost surface coextensive with and secured substantially continuously to substantially all of said non-object contacting surface of said uppermost layer, said discrete apertures in said second plane of said uppermost layer thereby directly exposing discrete portions of said moisture absorbent substrate to said soiled object when said absorbent structure and said object contact one another, said uppermost layer and the portions of said absorbent substrate secured thereto being resiliently deformable to permit the apertures in said uppermost layer which are located in said second plane to move closer to without becoming coplanar with those portions of said uppermost layer which are previous to moisture and which are located in said first plane when said absorbent structure and said soiled object contact one another at pressures of up to about 45 pounds per square inch (3.16 kilograms per square centimeter), yet move away from one another when said object and said absorbent structure separate from one another, whereby particulate is transferred into said absorbent substrate via said discrete apertures in said second plane and moisture is transferred into said absorbent substrate via said discrete apertures in said second plane and the fluid-pervious portions of said uppermost layer located in said first plane.

2. The disposable adsorbent structure of claim 1, wherein said uppermost layer is comprised of fluid-impervious material and said fluid-pervious portions of said uppermost layer located in said first plane comprise discrete apertures, whereby particulate is also transferred into said absorbent substrate via said discrete apertures in said first plane.

3. The disposable absorbent structure of claim 1 or claim 2, wherein said uppermost layer comprises a polymeric material.

4. The disposable absorbent structure of claim 3, wherein said uppermost layer comprises polyethylene.

5. The disposable absorbent structure of claim 1, wherein said uppermost layer is comprised of moisture-pervious material.

6. The disposable absorbent structure of claim 5, wherein said uppermost layer comprises a non-woven material.

7. The disposable absorbent structure of claim 5, wherein said fluid-pervious portions of said uppermost layer located in said first plane include discrete apertures.

8. The disposable absorbent structure of claim 1, wherein said upwardly extending protuberances comprise discrete enclosures.

9. The disposable absorbent structure of claim 8, wherein said discrete enclosures comprise conical segments.

10. The disposable absorbent structure of claim 8, wherein said discrete enclosures comprise pyramidal segments.

11. The disposable absorbent structure of claim 1, wherein said upwardly extending protuberances comprise ribs.

12. The disposable absorbent structure of claim 11, wherein said ribs are rectilinear along at least a portion of their length.

13. The disposable absorbent structure of claim 11, wherein said ribs are curvilinear along at least a portion of their length.

14. The disposable absorbent structure of claim 1, wherein said moisture absorbent substrate comprises a fibrous material.

15. The disposable absorbent structure of claim 14, wherein said moisture absorbent substrate comprises an airlaid, latex impregnated fibrous web.

16. The disposable absorbent structure of claim 15, wherein said airlaid, latex impregnated fibrous web exhibits a continuous pattern of densified areas across its surface.

17. The disposable absorbent structure of claim 1, including a moisture-impervious barrier layer secured in subjacent relation to the lowermost surface of said moisture absorbent substrate.

18. The disposable absorbent structure of claim 1, wherein said moisture-impervious barrier layer comprises a layer of polymeric film.

19. The disposable absorbent structure of claim 1, wherein said moisture-impervious barrier layer comprises a continuous layer of hot melt adhesive.

20. The disposable absorbent structure of claim 17, including a layer of resilient material adhered to the lowermost surface of said moisture-impervious barrier layer.

21. The disposable absorbent structure of claim 20, wherein said layer of resilient material is comprised of an open celled foam.

22. The disposable absorbent structure of claim 21, wherein said open celled foam is comprised of polyurethane.

23. The disposable absorbent structure of claim 21, including means on the lowermost surface of said foam to impart floor stability.

24. The disposable absorbent structure of claim 21, wherein said means to impart floor stability comprises a thin layer of pressure sensitive adhesive.

25. A disposable absorbent structure for removal and retention of moisture and particulate from a soiled object coming in contact therewith, said structure comprising:

(a) a three-dimensionally expanded, shear-resistant uppermost layer having an object contacting surface and a non-object contacting surface, said uppermost layer exhibiting a first pattern of protuberances originating in and extending upwardly from a first plane and terminating in a second plane substantially parallel to and remote from said first plane, said uppermost layer further exhibiting a multiplicity of discrete apertures in said first plane, said discrete apertures in said first plane being located intermediate said adjacent upwardly extending protuberances and defining the bases for a second pattern of protuberances originating in and extending downwardly from said first plane, said protuberances in said second pattern terminating in a third plane substantially parallel to and remote from said first plane, said uppermost layer being moisture-pervious in said third plane, said uppermost layer further exhibiting a multiplicity of discrete apertures in said second plane, said apertures in said second plane being located at the end of said protuberances terminating in said second plane; and (b) a moisture absorbent substrate having its uppermost surface coextensive with and secured substantially continuously to substantially all of said non-object contacting surface of said uppermost layer, said discrete apertures in said second plane of said uppermost layer thereby exposing the adjacent portions of said moisture absorbent substrate when said absorbent structure and said object contact one another, said uppermost layer and the portions of said absorbent substrate secured thereto being resiliently deformable to permit said discrete apertures in said uppermost layer which are located in said second plane to move closer to without becoming coplanar with said discrete apertures in said first plane when said absorbent structure and said soiled object contact one another at pressures of up to about 45 pounds per square inch (3.16 kilograms per square centimeter), yet move away from one another when said object and said absorbent structure separate from one another, whereby particulate is transferred from said soiled object into said moisture absorbent substrate via said discrete apertures in said second plane and moisture is transferred from said soiled object into said moisture absorbent substrate via said discrete apertures in said second plane and the moisture-pervious portions of said uppermost layer located in said third plane.

26. The disposable absorbent structure of claim 25, wherein said uppermost layer is comprised of fluid-impervious material and said fluid-pervious portions of said uppermost layer located in said third plane comprise discrete apertures, whereby particulate is also transferred into said absorbent substrate via said discrete apertures in said third plane.

27. The disposable absorbent structure of claim 25 or claim 26, wherein said uppermost layer comprises a polymeric material.

28. The disposable absorbent structure of claim 27, wherein said uppermost layer comprises polyethylene.

29. The disposable absorbent structure of claim 25, wherein said uppermost layer is comprised of moisture-pervious material.

30. The disposable absorbent structure of claim 29, wherein said uppermost layer comprises a non-woven material.

31. The disposable absorbent structure of claim 29, wherein said fluid-pervious portions of said uppermost layer located in said third plane include discrete apertures.

32. The disposable absorbent structure of claim 25, wherein said upwardly extending and said downwardly extending protuberances comprise discrete enclosures.

33. The disposable absorbent structure of claim 32, wherein said discrete enclosures comprise conical segments.

34. The disposable absorbent structure of claim 32, wherein said discrete enclosures comprise pyramidal segments.

35. The disposable absorbent structure of claim 25, wherein said upwardly extending protuberances comprise ribs.

36. The disposable absorbent structure of claim 35, wherein said ribs are rectilinear along at least a portion of their length.

37. The disposable absorbent structure of claim 35, wherein said ribs are curvilinear along at least a portion of their length.

38. The disposable absorbent structure of claim 25, wherein said moisture absorbent substrate comprises a fibrous material.

39. The disposable absorbent structure of claim 38, wherein said moisture absorbent substrate comprises an airlaid, latex impregnated fibrous web.

40. The disposable absorbent structure of claim 39, wherein said airlaid, latex impregnated fibrous web exhibits a continuous pattern of densified areas across its surface.

41. The disposable absorbent structure of claim 25, including a moisture-impervious barrier layer secured in subjacent relation to the lowermost surface of said moisture absorbent substrate.

42. The disposable absorbent structure of claim 25, wherein said moisture-impervious barrier layer comprises a layer of polymeric film.

43. The disposable absorbent structure of claim 25, wherein said moisture-impervious barrier layer comprises a continuous layer of hot melt adhesive.

44. The disposable absorbent structure of claim 41, including a layer of resilient material adhered to the lowermost surface of said moisture-impervious barrier layer.

45. The disposable absorbent structure of claim 44, wherein said layer of resilient material is comprised of an open celled foam.

46. The disposable absorbent structure of claim 45, wherein said open celled foam is comprised of polyurethane.

47. The disposable absorbent structure of claim 45, including means on the lowermost surface of said foam to impart floor stability.

48. The disposable absorbent structure of claim 45, wherein said means to impart floor stability comprises a thin layer of pressure sensitive adhesive.

49. A disposable absorbent floor mat structure for removal and retention of moisture and particulate from a soiled object coming in contact therewith, said structure comprising:

(a) a macroscopically patterned, three-dimensionally expanded, shear-resistant uppermost layer comprised of moisture-impervious material and having an object contacting surface and a non-object contacting surface, said uppermost layer exhibiting a pattern of protuberances originating in and extending upwardly from a first plane and terminating in a second plane substantially parallel to and remote from said first plane, said uppermost layer exhibiting a multiplicity of discrete apertures in said first plane intermediate adjacent protuberances, said uppermost layer further exhibiting a multiplicity of discrete apertures in said second plane, said apertures in said second plane being located at the terminal end of said protuberances originating in said first plane;

(b) a moisture absorbent substrate having its uppermost surface coextensive with and secured substantially continuously to substantially all of said non-object contacting surface of said uppermost layer, said discrete apertures in said uppermost layer thereby directly exposing discrete portions of said moisture absorbent substrate to said soiled object when said absorbent structure and said object contact one another, said uppermost layer and the portions of said absorbent substrate secured thereto being resiliently deformable to permit said discrete apertures in those portions of said uppermost layer which are located in said second plane to move closer to without becoming coplanar with said discrete apertures in those portions of said uppermost layer which are located in said first plane when said absorbent structure and said soiled object contact one another at pressures of up to about 45 pounds per square inch (3.16 kilograms per square centimeter), yet move away from one another when said object and said absorbent structure separate from one another, whereby moisture and particulate are transferred into said absorbent substrate via said discrete apertures located in said first and second planes;

(c) a moisture-impervious barrier layer secured subjacent said moisture absorbent substrate to prevent absorbed moisture from reaching the surface on which said floor mat is placed; and (d) a resilient layer secured subjacent said moisture-impervious barrier layer to promote overall conformance of said floor mat to the surface of soiled objects coming in contact therewith.

50. The disposable absorbent floor mat structure of claim 49, including means for imparting skid resistance to the lowermost surface of said resilient layer.

51. The disposable absorbent floor mat structure of claim 50, wherein said means for imparting skid resistance comprises a thin layer of pressure sensitive adhesive.

52. A disposable absorbent floor mat structure for removal and retention of moisture and particulate from a soiled object coming in contact therewith, said structure comprising:

(a) a three-dimensionally expanded, shear-resistant uppermost layer comprised of moisture-impervious material and having an object contacting surface and a non-object contacting surface, said uppermost layer exhibiting a first pattern of protuberances originating in and extending upwardly from a first plane and terminating in a second plane substantially parallel to and remote from said first plane, said uppermost layer further exhibiting a multiplicity of discrete apertures in said first plane, said discrete apertures in said first plane being located intermediate said adjacent upwardly extending protuberances and defining the bases for a second pattern of protuberances originating in and extending downwardly from said first plane, said protuberances in said second pattern terminating in a third plane substantially parallel to and remote from said first plane, said uppermost layer further exhibiting a multiplicity of discrete apertures in said second plane, and a multiplicity of discrete apertures in said third plane, said apertures in said second and third planes being located at the terminal ends of said upwardly extending and said downwardly extending protuberances;

(b) a moisture absorbent substrate having its uppermost surface coextensive with and secured substantially continuously to substantially all of said non-object contacting surface of said uppermost layer, said discrete apertures in said second and said third planes of said uppermost layer thereby exposing the adjacent portions of said moisture absorbent substrate when said absorbent structure and said object contact one another, said uppermost layer and the portions of said absorbent substrate secured thereto being resiliently deformable to permit said discrete apertures in said uppermost layer which are located in said second plane to move closer to without becoming coplanar with said discrete apertures in said uppermost layer which are located in said first plane when said absorbent structure and said soiled object contact one another at pressures of up to about 45 pounds per square inch (3.16 kilograms per square centimeter), yet move away from one another when said object and said absorbent structure separate from one another, whereby moisture and particulate are transferred from said soiled object into said moisture absorbent substrate via said discrete apertures in said second and third planes;

(c) a moisture-impervious barrier layer secured subjacent said moisture absorbent substrate to prevent absorbed moisture from reaching the surface on which said floor mat is placed; and (d) a resilient layer secured subjacent said moisture-impervious barrier layer to promote overall conformance of said floor mat to the surface of soiled objects coming in contact therewith.

53. The disposable absorbent floor mat structure of claim 52, including means for imparting skid resistance to the lowermost surface of said resilient layer.

54. The disposable absorbent floor mat structure of claim 53, wherein said means for imparting skid resistance comprises a thin layer of pressure sensitive adhesive.

* * * * *